US009572646B2

(12) United States Patent
Tapocik

(10) Patent No.: US 9,572,646 B2
(45) Date of Patent: Feb. 21, 2017

(54) ELECTRICAL PEN WITH IMPROVEMENTS FOR PEN REMOVABLY RETAINING SINGLE USE CARTRIDGE CONTAINING TOOTH WHITENING COMPOUNDS, DENTAL BONDING COMPOUNDS, NAIL POLISH, AND ADHESIVES AND REMOVABLY RETAINING DISPOSABLE TOOTH WHITENING APPLICATORS, DISPOSABLE DENTAL BONDING COMPOUND APPLICATORS, NAIL POLISH APPLICATORS AND DISPOSABLE ADHESIVE APPLICATORS

(71) Applicant: Bryan Tapocik, Highland, CA (US)

(72) Inventor: Bryan Tapocik, Highland, CA (US)

( * ) Notice: Subject to any disclaimer, the term of this patent is extended or adjusted under 35 U.S.C. 154(b) by 25 days.

(21) Appl. No.: 14/664,658

(22) Filed: Mar. 20, 2015

(65) Prior Publication Data
US 2016/0270893 A1    Sep. 22, 2016

(51) Int. Cl.
B05C 17/005    (2006.01)
A61C 19/06    (2006.01)
B05C 17/01    (2006.01)
A45D 40/26    (2006.01)

(52) U.S. Cl.
CPC ............ *A61C 19/066* (2013.01); *A45D 40/26* (2013.01); *B05C 17/00586* (2013.01); *B05C 17/0103* (2013.01); *A61C 19/063* (2013.01); *B05C 17/00559* (2013.01); *B05C 17/00566* (2013.01); *B05C 17/00596* (2013.01)

(58) Field of Classification Search
CPC ............ A61C 19/066; B05C 17/00566; B05C 17/00576; B05C 17/00596; B05C 17/01; B05C 17/0103

USPC ......... 401/40, 42, 44, 46, 47, 134, 137, 139, 401/150; 222/137, 145.5, 145.6, 333, 390; 178/18
See application file for complete search history.

(56) References Cited

U.S. PATENT DOCUMENTS

| | | |
|---|---|---|
| 4,121,739 A | 10/1978 | Devaney |
| 5,092,842 A | 3/1992 | Bechtold et al. |
| 5,104,005 A | 4/1992 | Schneider, Jr. |
| 5,310,091 A | 5/1994 | Dunning et al. |
| 5,333,760 A | 8/1994 | Simmen |
| 5,535,922 A | 7/1996 | Maziarz |
| 5,611,687 A | 3/1997 | Wagner |
| 5,743,436 A | 4/1998 | Wilcox et al. |
| 6,048,201 A | 4/2000 | Zwingenberger |
| 6,116,900 A | 9/2000 | Ostler |
| 6,176,632 B1 | 1/2001 | Kageyama et al. |

(Continued)

FOREIGN PATENT DOCUMENTS

| | | |
|---|---|---|
| JP | 096151123 A | 6/1997 |
| JP | 2007130437 A | 5/2007 |

*Primary Examiner* — David Walczak
*Assistant Examiner* — Joshua Wiljanen
(74) *Attorney, Agent, or Firm* — Thomas I Rozsa

(57) ABSTRACT

An apparatus for removably retaining a single use cartridge and dispensing at least one compound from the single use cartridge. The apparatus includes a dispensing pen having a housing which includes a source of electricity, an electric motor, a gear assembly and a moving shaft with a multiplicity of teeth to cause an advancing shaft to move forwardly toward the front of the pen and interact with a piston to push a plunger at the rear of the cartridge so that it will dispense compounds from the cartridge. The cartridge can be a single chamber cartridge or a dual chamber cartridge or a dual chamber cartridge separated by a dividing wall. There can be any numerous compounds including teeth whitening compounds, nail polish, cosmetics, etc.

23 Claims, 27 Drawing Sheets

(56) References Cited

U.S. PATENT DOCUMENTS

| | | |
|---|---|---|
| 6,227,739 B1 | 5/2001 | Kageyama |
| 6,283,660 B1 | 9/2001 | Furlong et al. |
| 6,918,515 B2 | 7/2005 | Noguchi |
| 7,201,527 B2 | 4/2007 | Thorpe et al. |
| 7,344,375 B2 | 3/2008 | Mukasa et al. |
| 7,748,980 B2 | 7/2010 | Mulhauser et al. |
| 7,794,166 B2 | 9/2010 | Zhang |
| 7,882,983 B2 | 2/2011 | Reidt et al. |
| 7,976,489 B2 | 7/2011 | Lawter et al. |
| 7,980,778 B2 | 7/2011 | Akaishi et al. |
| 8,096,449 B2 | 1/2012 | Keller |
| 8,328,449 B2 | 12/2012 | Wightman et al. |
| 2005/0063766 A1 | 3/2005 | Chen et al. |
| 2006/0275225 A1 | 12/2006 | Prencipe et al. |
| 2007/0086830 A1 | 4/2007 | Kageyama |
| 2008/0274066 A1 | 11/2008 | Montgomery |
| 2009/0095777 A1 | 4/2009 | Francavilla |
| 2009/0247915 A1 | 10/2009 | Imboden et al. |
| 2010/0114025 A1 | 5/2010 | Moller |
| 2010/0298781 A1 | 11/2010 | Hogdahl et al. |
| 2011/0129288 A1 | 6/2011 | Uehara | ial USE CARTRIDGE CONTAINING TOOTH WHITENING COMPOUNDS, DENTAL BONDING COMPOUNDS, NAIL POLISH, AND ADHESIVES AND REMOVABLY RETAINING DISPOSABLE TOOTH WHITENING APPLICATORS, DISPOSABLE DENTAL BONDING COMPOUND APPLICATORS, NAIL POLISH APPLICATORS AND DISPOSABLE ADHESIVE APPLICATORS

BACKGROUND OF THE INVENTION

1. Field of the Invention

This patent application contains alternative inventions/embodiments by the same inventor of co-pending utility patent application Ser. No. 14/087,401 filed on Nov. 22, 2013 and also co-pending utility patent application Ser. No. 14/609,355 filed on Jan. 29, 2015.

2. Description of the Prior Art

The following 26 patents and published patent applications are the closest prior art references which were uncovered in the search. A complete set of copies of these patents and patent applications are enclosed herewith for your review.

1. U.S. Pat. No. 5,611,687 issued to Eugene C. Wagner on Mar. 18, 1997 for "Oral Hygiene Delivery System" (hereafter the "Wagner Patent");

2. U.S. Pat. No. 6,176,632 issued to Hidehei Kageyama et al. on Jan. 23, 2001 for "Liquid Container" (hereafter the "'632 Kageyama Patent");

3. U.S. Pat. No. 6,227,739 issued to Hidehei Kageyama on May 8, 2001 for "Liquid Container" (hereafter the "'739 Kageyama Patent");

4. United States Published Patent Application No. 2005/0063766 to Sou Y. Chen et al. on Mar. 24, 2005 for "Applicator Pen" (hereafter the "Chen Published Patent Application");

5. U.S. Pat. No. 6,918,515 issued to Yoshio Noguchi on Jul. 19, 2005 for "Liquid Container" (hereafter the "Noguchi Patent");

6. United States Published Patent Application No. 2006/0275225 to Michael Prencipe et al. on Dec. 7, 2006 for "Applicator and Method For Applying A Tooth Whitening Composition" (hereafter the "Prencipe Published Patent Application");

7. U.S. Pat. No. 7,201,527 issued to Richard Christopher Thorpe et al. on Apr. 10, 2007 for "Twist Up Pen Type Dispenser With Brush Applicator" (hereafter the "Thorpe Patent");

8. United States Published Patent Application No. 2007/0086830 to Hidehei Kageyama on Apr. 19, 2007 for "Liquid Container" (hereafter the "Kageyama Published Patent Application");

9. United States Published Patent Application No. 2008/0274066 to Robert Eric Montgomery on Nov. 6, 2008 for "Compositions, Methods, Devices, And Kits for Maintaining or Enhancing Tooth Whitening" (hereafter the "Montgomery Published Patent Application").

10. U.S. Pat. No. 7,794,166 issued to Jun Zhang on Sep. 14, 2010 for "Press-Type Cosmetic Container with Anti-Press Means" (hereafter the "Zhang Patent");

11. United States Published Patent Application No. 2011/0129288 to Junya Uehara on Jun. 2, 2011 for "Liquid Applicator" (hereafter the "Uehara Published Patent Application");

12. U.S. Pat. No. 7,980,778 issued to Tetsuaki Akaishi et al. on Jul. 19, 2011 for "Liquid Applicator" (hereafter the Akaishi Patent");

13. U.S. Pat. No. 8,328,449 issued to James C. Wightman et al. on Dec. 11, 2012 for "Click Pen Applicator Device And Method of Using Same" (hereafter the "Wightman Patent");

14. Japanese Patent No. JP096151123A issued to Shiraishi Katsuhiko et al. on Jun. 10, 1997 for "Tooth Coating Liquid" (hereafter the "Katsuhiko Japanese Patent");

15. Japanese Patent No. JP2007130437A issued to Kageyama Shuhei on May 31, 2007 for "Liquid Container" (hereafter the "Shuhei Japanese Patent").

16. U.S. Pat. No. 4,121,739 issued to William David Devaney et al. on Oct. 24, 1978 for "Dispenser With Unitary Plunger And Seal Construction" (hereafter the "Devaney Patent");

17. U.S. Pat. No. 5,104,005 issued to Franz K. Schneider, Jr. et al. on Apr. 14, 1992 for "Dual Component Mechanically Operated Caulking Gun" (hereafter the "Schneider Patent");

18. U.S. Pat. No. 5,310,091 issued to Walter B. Dunning et al. on May 10, 1994 for "Dual Product Dispenser" (hereafter the "Dunning Patent");

19. U.S. Pat. No. 5,333,760 issued to Christen Simmen on Aug. 2, 1994 for "Dispensing And Mixing Apparatus" (hereafter the "Simmen Patent");

20. U.S. Pat. No. 5,535,922 issued to Bernard J. Maziarz on Jul. 16, 1996 for "Caulking Gun Dispensing Module For Multi-Component Cartridge" (hereafter the "Maziarz Patent");

21. U.S. Pat. No. 6,116,900 issued to Calvin D. Ostler on Sep. 12, 2000 for "Binary Energizer And Peroxide Delivery System For Dental Bleaching" (hereafter the "Ostler Patent");

22. U.S. Pat. No. 6,283,660 issued to Patrick J. Furlong et al. on Sep. 4, 2001 for "Pen Dispensing And Cartridge System" (hereafter the "Furlong Patent");

23. United States Published Patent Application No. 2009/0095777 to Frank Francavilla on Apr. 16, 2009 for "Dispensing Pen" (hereafter the "Francavilla Published Patent Application");

24. U.S. Pat. No. 7,748,980 issued to Paul Mulhauser et al. on Jul. 6, 2010 for "Dispenser for Dental Compositions" (hereafter the "Mulhauser Patent");

25. U.S. Pat. No. 7,882,983 issued to Dean K. Reidt et al. on Feb. 8, 2011 for "Capsule for Two-Component Materials" (hereafter the "Reidt Patent");

26. U.S. Pat. No. 8,096,449 issued to Wilheilm A. Keller on Jan. 17, 2012 for "Dispensing Appliance for a Multiple Cartridge" (hereafter the "Keller Patent").

The Wagner Patent discloses:

"A delivery system for a liquid oral hygiene preparation suitable for tooth whitening, tooth cleansing and the treatment of. The delivery system includes an elongate barrel shaped body. A supply of the hygiene preparation saturates a fibrous wadding carried in a hollow chamber of the body. At an end of the body, an applicator formed of felt or synthetic fibers is seated. The applicator includes a broad tip and a stem wick which is received in the wadding and draws the preparation to the tip by capillary action. The preparation is applied to tooth surfaces, oral lesions, and the like by pressing the tip against the surface to receive the preparation and, where appropriate, wiping the tip along the surface. In an alternate embodiment, ball applicator is provided and the hygienic preparation may be carried in the chamber without the wadding."

The '632 Kageyama discloses:

"A liquid container such that the liquid received in it will not easily spring out from its tip even if it is wrongly operated, comprises a tank portion for receiving a liquid, a knock bar stretching axially movably within the tank portion which is designed to have on its axial tip portion a pump shelf portion whose diameter have been enlarged, an induction bar fixed into the tip of the knock bar, a brush provided on the tip side of the induction bar, and a spring for always energizing the above knock bar and induction bar rearward. On the internal periphery surface of the above tank portion, a plurality of ribs are formed which stretch axially and on top of which the above pump shelf portion can slide, the internal periphery surface ahead of the ribs is at the same level as and continuous with the top face of the ribs and designed as a diameter-reducing portion where the pump shelf portion can slide. The pump shelf portion slidably touches the ribs when it is not biased."

The '739 Kageyama Patent is related to the previously discussed patent and discloses:

"A liquid container includes a body having a tank portion housing liquid, and a liquid supply port at a front side thereof, a piston moving forward inside the tank portion, a piston rod being integrally connected to the piston and extending rearward, the piston rod having an external thread formed in a periphery thereof, an operation cylinder being attached to a rear part of the body in a relatively rotatable fashion, a piston rod guide being adapted to be rotated integrally with the operating cylinder, the piston rod guide having an internal thread hole which is engaged with the external thread of the piston rod, and a ratchet cylinder being fixed in the rear inside the body, the ratchet cylinder having a bore through which the piston rod is pierced in a relatively unrotatable fashion. The operation cylinder is formed with serrated gear teeth at a front end thereof, and the ratchet cylinder is formed with a ratchet gear tooth which is brought into engagement with the serrated gear teeth and adopted to be selectively protruded or retracted in an axial direction, at a rear end thereof."

The Chen Published Patent Application discloses:

"FIG. 1 is a cross-sectional view of an applicator pen 100 according to a first embodiment. The applicator pen 100 is formed of a number of different sub-assemblies that are then combined in an engaging manner to form the applicator pen 100. More specifically, the applicator pen 100 includes a body 110 and an applicator assembly 200 that serves to restrict and disperse an applicator material 112 that is stored within the body 110. The applicator pen 100 also includes a drive mechanism 300 for advancing the applicator material 112 within the body 110 such that it is introduced into and dispersed through the applicator assembly 200 to the consumer. The drive mechanism 300 is coupled to a button assembly 400 that permits the consumer to simply advance the applicator material 112 an incremental amount within the body 110 upon manipulation of the button assembly 400, e.g., a press and release action of the button assembly 400.

While the applicator material 112 can be any number of different types of materials, it will be appreciated that one exemplary use of the applicator 100 is as a cosmetic applicator and therefore, in this particular use, the applicator material 112 is in the form of a cosmetic product. For example, the applicator material 112 can in the form of conventional make-up, such as an eye shadow or liner, lipstick, other facial products, etc. The applicator material 112 is typically a viscous material, such as a liquid, gel or other material that has some flow properties."

The focus of this patent application is primarily a cosmetic applicator for eyeshadow, a liner, etc. and not for teeth whitening.

The Noguchi Patent discloses:

"In a liquid container, the dimension of inside diameter of a liquid supply portion is not subject to any restriction, and also a liquid leakage suppressing mechanism that is not subject to any restriction by the viscosity of stored liquid is provided. A liquid container includes a body having a tank for storing a liquid; a supply mechanism which is connected to the tip end portion of the body and has a brush for supplying the liquid; and a drive mechanism for pushing out the liquid L in the tank T to the supply mechanism. A valve which is normally closed and can be opened only when the drive mechanism is operated is provided between the tank and the supply mechanism."

The Prencipe Published Patent Application discloses:

"The dispenser 10 is shown as a complete unit in FIGS. 1 and 2. The dispenser is comprised of three sections. These are an applicator section 12, a whitening product storage section 14 and a dispenser drive section 16. The applicator section is comprised of an overcap 18, an applicator surface 30, an applicator surface holder 32, an applicator mounting unit 36 and a delivery channel 34 The whitening product in product chamber 40 is delivered to the applicator surface through delivery channel 34. A tubular wall 20 forms the product chamber 40. Piston 42 forms the upper wall of product chamber 40.

The dispenser drive section 16 is comprised of the mechanism to advance piston 42 downward in whitening product chamber 40. This dispenser drive section is shown in more detail in FIG. 5. Rotating unit 22 will rotate while tubular wall 20 of the whitening product chamber is stationary.

FIG. 7 shows an applicator tip with a fibrillated surface The applicator tip is comprised of channel 60 having a cross-section 65 which receives the peroxide containing tooth whitening composition from storage chamber 40. Fibrillated surface 62 is the application surface to apply the composition to the teeth. The peroxide tooth whitening composition flows through opening 64 of the channel 60. Applicator surface holder 66 holds channel 60 and is in turn held in place by applicator mounting unit 68. FIG. 8 is an exploded view of the applicator tip of FIG. 7. Additionally shown in this view is a chamber 70 on the applicator surface holder channel 72 of the applicator mounting unit 68. Flange 74 holds the applicator surface holder 66 in applicator mounting unit 68."

The Dwyer Published Patent Application discloses:

"A method for manufacturing a cosmetic product applicator assembly includes selecting a disposable handle having a desired design from a number of handles of various designs. Each of the handles includes an elongated, decorative housing with a first end having an opening, a hollow chamber extending from the opening into the housing, and a flattened portion for displaying a word, phrase, symbol or design. A cosmetic product applicator having a first terminal end from which the cosmetic product is dispensed and a second terminal end opposite the first terminal end is inserted into the handle. The hollow chamber is adapted to receive and engage the second terminal end of the applicator in a non-rotatable manner."

The Thorpe Patent discloses:

"As shown in FIGS. 2 and 5, the twist up pen type dispenser with brush applicator 1 comprises a body 2, preferably substantially in the shape of a cylinder, having a top 3, a bottom 4, an outer surface 5 and an inner surface 6 which defines an annular space 7. As shown in FIGS. 4 and 5, material 8 may be within the annular space 7, which functions as a reservoir for the material 8 within the twist up pen type dispenser with brush applicator 1. The material 8 may be a dentifrice, such as tooth gel, tooth paste, mouthwash, mouth rinse, tooth whitener and combinations thereof, cosmetics, such as mascara and eyeliner, hair colorants such as darkeners, like darkeners for facial hair such as moustaches, dyes or similar materials, or skin treatment compositions, combinations thereof, and the like."

The Kageyama Published Patent Application discloses:

"To provide a liquid container which includes a liquid supply member that is exchangeably mounted thereto and prevents liquids in liquid supply members from being mixed each other after exchanging the liquid supply members. The liquid container is provided which includes a container body with a tank section to hold a liquid, an applicator coupled to the front end of the container body, a piston which is advanced through the tank section, and a piston advancing mechanism which has a pushing member and causes the piston to be advanced through the tank section in response to the operation of the pushing member. The applicator is removably coupled to the container body, and the piston advancing mechanism causes the piston to be moved only forward."

The Montgomery Published Patent Application discloses:

"The first and/or second tooth whitening compositions are preferably disposed in a delivery (e.g., FIGS. 2-4, 9, and 10), such as a dispensing tube, pencil, pen or liquid stick having an applicator 12, such as a felt tip 14 (FIG. 3), brush 16 (FIG. 4), roller ball, or non-woven pad. In one embodiment, the delivery device 10 includes more than one applicator 12 that may be removably engaged with the device 10. In an embodiment wherein the device 10 is a pen or a pencil, the applicator 12 may be retractable and/or housed in a cap 18. The tooth whitening compositions of the present invention may be housed directly within a reservoir 20 in the device 10 or may be supplied in a removable cartridge (not shown) within the reservoir 20 that may be replaced or refilled. The delivery device 10 may dispense the tooth whitening composition through a transfer channel 21 through capillary action, such as in a flow through pen, or through an actuator 22, such as mechanical piston with a click mechanism, twist button and ratchet mechanism, or pushbutton mechanism, or through a vacuum method of ejection, or through other such mechanical means for transferring the composition from the device to an oral cavity surface in need of treatment. The actuator 22 may be present on first end 24 of the device 10 and the applicator on a second end 26 of the device 10 or the actuator 22 may be present on a side wall 28 of the device. In one embodiment, the delivery device 10 includes a felt tip 14 or brush 16 applicator 12 wherein the inventive composition is dispensed to the applicator 12 through actuation of the actuator 22, such as by a clicking or twisting mechanism. Kotobuke Pencil, Japan, is one manufacturer of such types of delivery devices 10 (see, e.g., U.S. Pat. No. 6,176,632)."

The Zhang Patent discloses:

"The present invention is related to a press-type cosmetic container with an anti-press means. That is, a cosmetic container adopts the way of pressing to output the material therein. More particularly, the press cover of the cosmetic container is stopped by a block to prevent discharging or leaking the material in the cosmetic container."

Claim 1 of the patent reads as follows:

"A press-type cosmetic container with an anti-press means comprising: a tube member having a sleeve at the one end thereof, the outer edge of the sleeve being disposed a collar base; a rotating tube member being disposed a female ringing slot at the inner edge of the one end thereof, the rotating tube member being female-connected to the outer edge of the sleeve and the collar base of the tube member being slid on the female ringing slot so as to make the rotating tube member be turned around on the sleeve, wherein two axial extending ribs are disposed at the inner wall of the another end of the rotating tube member, a block is disposed between the two ribs, and a resisting member is disposed beside the two ribs; a press cover having two wedging member being extended outwardly and disposed on the two side edges thereof respectively, the one end of the press cover located at the wedging member being embedded at the inner edge of the free end of the rotating tube member, and the one wedging member being disposed beyond the two ribs; herein the block stops pressing the press cover in order to stop outputting material in the cosmetic container and then achieve the function of preventing improper pressing, and the rotating tube member is then turned around, the two wedging members are moved to locations beside the resisting member so as to output the material."

The Uehara Published Patent Application discloses:

"The present invention is a liquid applicator which, in its assembled state an applying part, joint, and front barrel are fixed to a barrel body front end portion, the step of an indented/projected engaging portion on the inner peripheral side of the applying part rear end portion is abutted from behind against and engaged with the step of an indented/projected engaging portion on the outer peripheral side of the forward part of the joint. At the same time, an indented/projected engaging portion on the outer peripheral side of the applying part rear end portion is abutted against and engaged with an indented/projected engaging portion on the inner peripheral side of the front barrel's forward part, and an indented/projected engaging portion on the inner peripheral side of the front barrel rearward part is engaged with an indented/projected engaging portion on the outer peripheral side in the rearward part of joint, whereby applying part, joint and front barrel are formed so as to fix the applying part to barrel body by means of the joint and the front barrel."

The Akaishi Patent discloses:

"A liquid applicator includes a liquid pressing mechanism 6 for pressurizing an application liquid 4 inside a main body 2 so as to supply the application liquid to an applying member 10 at the front end by the pressing of liquid pressing mechanism 6, wherein the applying member 10 is made of an elastic material, has a valve structure 8 which is formed with a communication path 24 for communication between the inside and outside of main body 2 and can close the communication path 24 by elasticity in the normal condition and open the communication path 24 by elastic deformation of the communication path when the application liquid is pressurized by liquid pressing mechanism 6, and, an ejection opening 24a of communication path 24 of valve structure 8 is arranged to front onto the applying portion 10a of the applying member 10."

The Wrightman Patent discloses:

"A click pen applicator device that provides predetermined dosing of the formulation for precise application, and rapidly primes the formulation using the dosing click mechanism to prepare the applicator for use."

Claim 1 of the patent reads as follows:

"A device for dispensing a formulation comprising: a centerband having a proximal end and a distal end and defining a storage section having the formulation disposed within; an applicator section situated at the distal end of the centerband; and a multistage actuator section situated at the proximal end of the centerband for rapid priming with a click dispensing mechanism with a piston seat having two sets of external threads on a shaft with an unthreaded length therebetween."

The Katsuhiko Japanese Patent discloses:

"PROBLEM TO BE SOLVED: To obtain a coating liquid capable of coloring tooth or tooth crowns to white or any other color by using an acrylic resin prepared by neutralizing an acrylic ester-methacrylic eater-based copolymer with a specific compound. SOLUTION: This tooth coating liquid contusions ethanol and an acrylic resin prepared by neutralizing an acrylic ester-methacrylic ester-based copolymer with 2-amino-2-methyl-1,3-propanediol or 2-amino-2-methyl-1-propanol, and may also contain a color pigment or extender pigment, and furthermore, ceramic(s) and/or a vinyl acetate resin. It is preferable that this coating liquid comprises 10-94.8 wt. % or more of ethanol, 0.1-30 wt. % of a pigment, 0.1-20 wt. % of the above acrylic resin, and 5-30 wt. % of ceramic(s) and/or butyl acetate resin. The pigment is pref. titanium dioxide (optimally, ≦100 nm primary particle diameter on average)."

The Shuhei Japanese Patent discloses:

"PROBLEM TO BE SOLVED: To provide a liquid container which includes a liquid supply member that is exchangeably mounted thereto and prevents liquids in liquid supply members from being mixed each other before and after exchanging the liquid supply members; SOLUTION: The liquid container includes a container body 12 with a tank section T to hold a liquid, an applicator 20 coupled to the front end of the container body 12, a piston 22 which is advanced through the tank section T, and a piston pressing mechanism 23 which has a knocking member 32 and causes the piston 22 to be pressed through the tank section T in response to the operation of the knocking member 32. The applicator 20 is removably coupled to the container body 12, and the piston pressing mechanism 23 causes the piston 22 to be moved only forward."

The Devaney Patent discloses:

"A dispenser for precisely metering viscous fluids from a cartridge. The dispenser includes a cartridge body and a plunger having a piston head at its extremity. The plunger is unitarily configured from a plastic material, including seal rings in the piston head. Each piston head including two such seal rings axially spaced from one another and configured to include sharp peripheral edges permitting resilient wedging contact within the bore of the cartridge."

The Schneider Patent discloses:

"A dual component caulking gun which utilizes a gun body to which there is affixed a dual component cartridge assembly designed to carry dual component cartridges. A ball screw is journaled within the gun body for rotary motion but locked against axial motion and extends in a direction opposite the component cartridge assembly. A pair of ram rods are journaled through the gun body and terminate at the first end in ejector rams and at their opposite end in a transfer bar that is interconnected to the ball screw by means of a ball screw nut."

The Dunning Patent discloses

"A dispenser for simultaneously dispensing and mixing a pair of fluid products such as chemically reactive resins, from a pair of axial adjacent front and rear chambers. A piston is mounted within each of the chambers and is moveable with respect to the hollow interior of the respective chamber for dispensing the fluid product therefrom. Telescopic movement of the rear chamber within the front chamber moves the pistons synchronously through the chambers to provide for controlled discharge of the products through a front discharge nozzle. A fixed hollow delivery tube extends through the interior of the front chamber and telescopically receives therein a post which is mounted on a rear wall of the rear chamber. The rear chamber has a relatively tight sliding fit within the front chamber so that a partial vacuum is formed within an annular space which forms between the two pistons as they move apart upon discharge of the two products to produce a "suck back" effect on product remaining in the discharge nozzle."

The Simmen Patent discloses:

"A dispensing and mixing apparatus for simultaneously dispensing from a cartridge into a static mixing element components which harden when mixed. The components exit the cartridge into the mixing element without intermixing as the components leave the cartridge. The initial intermixing of the components takes place within the mixing element. The cartridge is reusable since the components do not become mixed and harden as they come out of the cartridge. The chambers in the cartridge are of semi-cylindrical configuration and have rounded corners. Ribs can be provided on the cartridge for stiffening the cartridge from deforming under extrusion."

The Maziarz Patent discloses:

"The invention provides a dispensing module for dispensing multi-part adhesive from a multi-component cartridge utilizing a standard caulking gun. The dispensing module comprises a piston actuator and a module housing which when assembled with a standard multi-component cartridge and inserted into a standard caulking gun allows the components from the multi-component cartridge to be dispensed."

The Ostler Patent discloses:

"A dental bleach storage, mixing and delivery device and related method are disclosed. The device includes a barrel with at least two chambers. The chambers store components that when mixed can form a dental bleach or whitener. A plunger is provided that can be reciprocated within the barrel to force such components from their chambers. A mixing tip is provided for the end of the barrel. The components may be forced through the mixing tip which thoroughly mixes them together. The resulting bleach or whitener is applied to a patient's teeth where oxygen ions released from the bleach or whitener and will whiten the patient's teeth."

The Furlong Patent is a pen dispensing cartridge system which issued in 2001 and is still in full force and effect. The patent discloses:

"The present invention features a pen used, for example, to dispense nail polish for finger nail application. The design is for a unit of use, meaning that the preferred pen uses cartridges, i.e., units. In a preferred embodiment, each cartridge is filled with polish and has a brush head. After the cartridge is used, the user simply disposes of the old cartridge and replaces it with a new cartridge for the next application."

The Francavilla discloses:

"The present invention is related to a dispensing device. The dispensing device includes a container; a dispensing opening located at one end of the container; a plunger located inside the container; a pushbutton associated with the plunger; and a drive mechanism configured to drive the plunger linearly inside the container from a first position towards the dispensing opening when the pushbutton is pressed and to hold the plunger at a second position, wherein the second position is closer to the dispensing opening than the first position."

The Reidt Patent discloses:

"Capsule (10) for two or more components of a material which are to be mixed together, comprising a cartridge (11) comprising an outlet (12), a first component chamber (13) for containing a first component, and a second component chamber (14) for containing a second component, the two chambers (13, 14) opening into the outlet (12); and a piston (15) which at least with its front end sits in the cartridge (11), lies with its rear end outside the component chambers (13, 14) and, when it is pushed forwards, presses the two components out of their component chambers (13, 14)."

The Mulhauser Patent discloses a dispenser for dental compositions.

Claim 1 of this patent reads as follows:

"An apparatus for dispensing dental compositions, the apparatus comprising: a) a body comprising a top shell portion, a bottom shell portion, and a chamber received therein; b) a replaceable cartridge having at least two lumens with at least two pistons, the cartridge operable to dispense a component of a dental compound contained within the lumens, and wherein the cartridge is further operable to be at least partially inserted into the chamber; c) an inner mechanical system disposed in the body, the inner mechanical system comprising a rack system, said rack system having at least two racks operable to be urged forward to engage a piston in each lumen of the cartridge; d) a button system in contact with the body, the button system operable to be depressed in a direction substantially forward and in line with the rack system by a user such that the button system engages the inner mechanical system when depressed, such that the rack is advanced a predetermined distance such that a metered amount of the components of the dental compound is dispensed from the at least two lumens; and e) wherein the inner mechanical system further comprises a plurality of teeth disposed on the rack system, and a drive spring and a pawl spring disposed on the body, the drive spring and the pawl spring being operable to interface with at least one of a plurality of teeth on the rack system and at least one surface of the button system such that depression of the button system by a user initiates drive spring to advance the rack system a predetermined distance proportional to the distance between a first selected tooth located on the rack and a second selected tooth located on the rack and initiates the pawl spring to disengage from a third selected tooth on the rack and engage a fourth selected tooth on the rack located at a distance substantially equal to the distance between the first tooth and the second tooth, and release of the button causes the drive spring to disengage from said first selected tooth and engage the second selected tooth on the rack."

The Keller Patent discloses a dispensing appliance for a multiple cartridge. The broadest claim is claim 1 which reads as follows:

"A dispensing appliance for a multiple cartridge or syringe, comprising: a housing configured to receive the multiple cartridge or syringe, and wherein the housing has a housing thread and a rotatable portion that has a complementary thread, wherein the housing thread and the rotatable portion cooperate in such a manner that by a mutual rotation of the housing thread and the rotatable portion, the rotatable portion is continuously displaceable relative to the housing in a dispensing direction, wherein the housing is configured to receive the multiple cartridge or syringe having at least two adjacent and parallel storage containers, wherein a thrust force of the rotatable portion is transmitted to a multiple ram with a single thrust plate, and wherein the multiple ram slides in the at least two adjacent and parallel storage containers of the multiple cartridge or syringe and the thrust plate is non-rotatably guided inside the housing."

The following additional patents and patent publication are of record in co-pending patent application Ser. No. 14/087,401:

United States Published Patent Publication No. 2010/0114025 to Claus Schmidt Moller published on May 6, 2010.

United States Published Patent Publication No. 2009/0247915 to IMBODEN et al. published on Oct. 1, 2009.

United States Published Patent Publication No. 2010/0298781 to Hogdahl et al. published on Nov. 25, 2010.

U.S. Pat. No. 7,976,489 issued to Lawter et al. on Jul. 12, 2011.

U.S. Pat. No. 5,092,842 issued to Bechtold et al. on Mar. 3, 1992.

U.S. Pat. No. 6,048,201 issued to Arthur Zwingenberger on Apr. 11, 2000.

U.S. Pat. No. 7,344,375 issued to Mukasa et al. on Mar. 18, 2008.

U.S. Pat. No. 5,7943,436 issued to Wilcox et al. on Apr. 4, 1998.

There is a significant need for an improved apparatus to dispense compounds including but not limited to tooth whitening compounds where the tooth whitening compounds are dispensed from a new and unused retainers. There is also a significant need for an improved apparatus to dispense dental bonding compounds from new and unused retainers and adhesive compounds from new and unused retainers. There is also a significant need for improved applicators for many other products such as nail polish and adhesive.

SUMMARY OF THE INVENTION

The present invention involves the field of numerous types of compounds which by way of example includes tooth whitening compounds and in particular, to specific apparatus which are used to retain tooth whitening compounds and then dispense them either into a dental tray where the tray is placed over the patient's teeth for a period of time or the tooth whitening compound is directly applied to the patient's teeth by the dentist or the dental assistant. More broadly described, the present invention includes compounds and applicators used to dispense the compounds including tooth whitening compounds, dental bonding and filling compounds, adhesives such as glue, finely ground powder, jells, creams, paints, cosmetics, lipstick, non-medicated cosmetics, medicated cosmetics, construction material compounds, and virtually any substance that has a sufficient viscosity to be pushed through a dispensing cartridge in a dispensing pen and either out of the cartridge, from the cartridge into an applicator, or from the cartridge into a mixing chamber and then out of the mixing chamber primarily into an applicator, which are hereafter jointly referred to in this patent application as "compounds".

The cartridges have either a single interior chamber or two interior chambers where the dual or two chambers are separated by a dividing wall. For a compound that does not require mixing, a single compound in a single interior chamber cartridge is used. Where two compounds are divided and only mixed immediately before use, the dual interior chamber cartridge is used.

Although the summary discussed below relates to tooth whitening compounds in detail, it is understood that the present invention includes all products defined above as compounds and is not limited to tooth whitening compounds.

The present invention involves a dispensing pen which removably retains a single use cartridge containing tooth whitening compound and removably retains disposable tooth whitening applicators. One of the major problems with prior art tooth whitening applicators is that the applicator itself is reused over and over again through syringes which contain the tooth whitening compound and even though they are sterilized, run the risk of transmitting disease from one patient to another. Therefore, there is a significant need for an improved tooth whitening apparatus where the cartridge containing the tooth whitening compound or compounds is disposable and replaceable with a new clean cartridge with a fresh supply of tooth whitening compound or compounds and the applicator heads which are used to apply the compounds to teeth or to a dental tray are also disposable and replaced with new applicators so that the patient receives a completely new and sterile system for the purpose of applying tooth whitening compounds. The only portion of the apparatus which is reused is the retaining pen which is used to removably retain the tooth whitening compound and to removably retain the tooth whitening applicators.

The variations of the embodiments of the present invention involve two variations on the interior of the single use cartridge. The variations of the embodiments of the present invention also involve the location of the single use cartridge.

In one embodiment of the present invention, the interior chamber of the unidose single use cartridge contains tooth whitening compound in a sealed condition with a cap that has an openings which is sealed by a frangible opening which seals the cartridge until it is ready for use and a screw on cap which contains at a remote end a piercing object to pierce the frangible seal so that the tooth whitening compound can be dispensed from the cartridge. In one variation, the cartridge has a single interior chamber so that the tooth whitening compound does not require any mixing before the tooth whitening compound is dispensed from the cartridge. For this variation, the rear of the interior chamber of the cartridge contains a single plunger having a pair of spaced apart sidewalls forming a seal against the interior sidewall of the cartridge. The rear of the plunger also includes a single pocket which receives a pushing piston from the retaining pen. The pushing piston is incrementally moved in a forward direction within the pen by an improved electrical mechanism of the present invention. The pushing piston engages and pushes the single pocket in the rear of the single plunger to push the compound out of the cartridge through an opening in a front nozzle of the cartridge after a seal on the nozzle is opened. In one sub-variation of this embodiment, the cartridge is retained within an interior chamber of the pen with the nozzle extending through a front opening in the pen. In another sub-variation, the front of the pen has a threaded exterior sidewall with male threads adjacent the front of the pen and the cartridge has mating interior female threads by which the cartridge is threaded onto the front of the pen and extends from the front of the pen and is exterior to the pen. There is still a similar sealing configuration on the rear of the cartridge which has a pocket against which the single piston pushes. In this sub-variation, the single pocket in the sealing plunger extends out of the pen into the exterior cartridge. The same new and novel electrical mechanism pushes the piston in increments to push the plunger which pushes the whitening compound out of the opening in the nozzle.

In an alternative embodiment of the present invention, the interior chamber of the unidose single use cartridge also contains tooth whitening compound in a sealed condition with a cap that has an openings which is sealed by a frangible opening which seals the cartridge until it is ready for use and a screw on cap which contains at a remote end a piercing object to pierce the frangible seal so that the tooth whitening compound can be dispensed from the cartridge. In the alternative variation, the cartridge has an interior longitudinal dividing wall with separate tooth whitening compounds in each chamber bounded by an interior surface of the cartridge and the dividing wall. The divided interior chamber retains two separate compounds which are separated from each other while in the cartridge by the a dividing wall. The interior rear of the cartridge has a different plunger having opposing interior faces to push a compound in a respective portion of the interior of the cartridge forward and out of the cartridge, and a pair of opposed angular sidewalls ending in rear wall sidewalls forming a seal against the interior sidewall of the cartridge. Each rear end of the plunger has a pocket to receive a respective pushing piston from a dual piston mechanism in the retaining pen. The interior chamber is divided into two equal chambers which contain different compounds which cannot come in contact with each other because the dividing wall extends for the entire diameter and length of the interior chamber of the cartridge. For dual compounds where less is needed of one of the two compounds, the dividing wall is thicker on one side to reduce the volume of compound in the smaller chamber, the design of the plunger is modified to accommodate the revised sidewall. For the operating mechanism for the dual chamber cartridge, the mechanism includes a pair of pistons which are respectively used to engage a respective pocket of the two-pocket plunger used with the dual chamber cartridge and a novel electrical mechanism to incrementally move each pushing piston in a forward direction within the pen. The pushing pistons respectively engage and push a respective one of the two pockets in the rear of the dual plunger to push the compounds out of the cartridge through an opening in a front nozzle of the cartridge after a seal on the nozzle is opened. After the compounds are pushed out of the cartridge, they are mixed in a mixing chamber before being dispensed. In one sub-variation of this embodiment, the cartridge is retained within an interior chamber of the pen with the nozzle extending through a front opening in the pen. In another sub-variation, the front of the pen has a threaded exterior sidewall with male threads adjacent the front of the pen and the cartridge has mating interior female threads by which the cartridge is threaded onto the front of the pen and extends from the front of the pen and is exterior to the pen. There is still a similar sealing configuration on the rear of the cartridge with the dual pistons respectively pushing against a respective one of the two pockets in the sealing plunger which now extends out of the pen into the exterior cartridge. The same new and novel electrical mechanism pushes the pistons in increments to push the plunger which pushes the whitening compound out of the opening in the nozzle into the mixing chamber.

An additional significant improvement of the present invention is the combination electrical motor gear assembly and movement shaft and advancing shaft which enable the compound from a unidose cartridge affixed either within a chamber within the dispensing pen or threaded on or affixed onto an exterior of the dispensing pen to be dispensed from the cartridge. The operating mechanism includes an electrical motor which then is connected to a gear assembly which has gears which advance in one direction or an opposite direction depending upon the circuitry closed. The gears in turn are connected to a movement shaft having teeth thereon through the entire length of the movement shaft which in turn is connected to a connecting box which is affixed to a rear end of an advancing shaft. A printed circuit board connected to the electricity activation members or pushbuttons can be programmed so that when an activation member or pushbutton is activated, the electric motor will rotate, the movement shaft will rotate in a given direction with its teeth interacting with teeth in the connecting box to cause the connecting box to move in a direction toward the front of the dispensing pen. The connecting box is also attached to the rear of the advancing shaft which is also further caused to move toward the front of the dispensing pen which advancing shaft is connected to a single plunger for a single compound cartridge or a dual plunger for a dual compound cartridge so that as the advancing shaft is caused to move incrementally toward the front of the dispensing pen, its affixed piston interacts with a pocket of a plunger in the unidose cartridge and will enable the compound to be pushed out of the cartridge and into either a receptacle or a mixing chamber depending upon the nature of the unidose cartridge used. The electrical mechanism is powered by a source of electricity which preferably is at least one battery and an electrical connection with a transformer reducing an electrical input and a motor to 100 DC voltage.

After the compound, whether single or mixed dual is dispensed, it extends to an applicator. With respect to alternative embodiments of the applicators, one embodiment is a straight applicator which is generally frustum shaped having a narrow dispensing tip and a threaded end which is threaded onto either the threaded end of the mixing tip or a threaded end of the cartridge and through which the tooth whitening compound flows and can be placed either into a dental tray or onto a patient's teeth.

In an alternative embodiment of the applicator, the applicator is horn-shaped or bent so that the tooth whitening compound can be directly applied to locations in the patient's mouth where teeth are near the back of the mouth, either upper or lower teeth and usually on the exterior but if necessary, also on the top or interior of the tooth.

In an alternative embodiment of the applicator, the applicator has an opening with a brush so that the tooth whitening compound extends through the applicator opening and then the brush is used to apply the tooth whitening compound onto the patient's tooth.

It is a primary object of the present invention to provide a single use cartridge and single use applicator so that tooth whitening compounds which are contained in the cartridge are used only once and the applicators used to apply the tooth whitening compound are also used only once and then discarded and replaced with a separate tooth whitening compound retaining cartridge and also replaced with separate applicator heads.

It is a further object of the present invention to provide a single use cartridge which contains a single compound which does not need to be mixed with any other compound and can simply be dispensed once the sealed cartridge is opened to dispense the tooth whitening compound onto teeth or onto a dental tray where it can be used.

It is a further object of the present invention to provide a single use cartridge which has a dividing wall so that the cartridge contains two separate compounds which are separated from each other and which may either have equal amounts of compounds on either side of the dividing wall or different amounts of compound where one compound is less than the other compound depending upon the formulation required for that tooth whitening application and then the compounds are mixed when they enter a chamber for mixing purposes.

It is the primary object of the present invention to provide a non-reusable cartridge and non-reusable applicator head so that a fresh cartridge containing fresh tooth whitening compounds, fresh dental bonding and filling compounds and adhesive compounds and fresh new applicators are used every time a new compound is dispensed so that a compound is not reused from one patient to another or from one adhesive bonding application to another, thereby providing safety and health to subsequent patients and products.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF PREFERRED EMBODIMENTS

Figure 1:
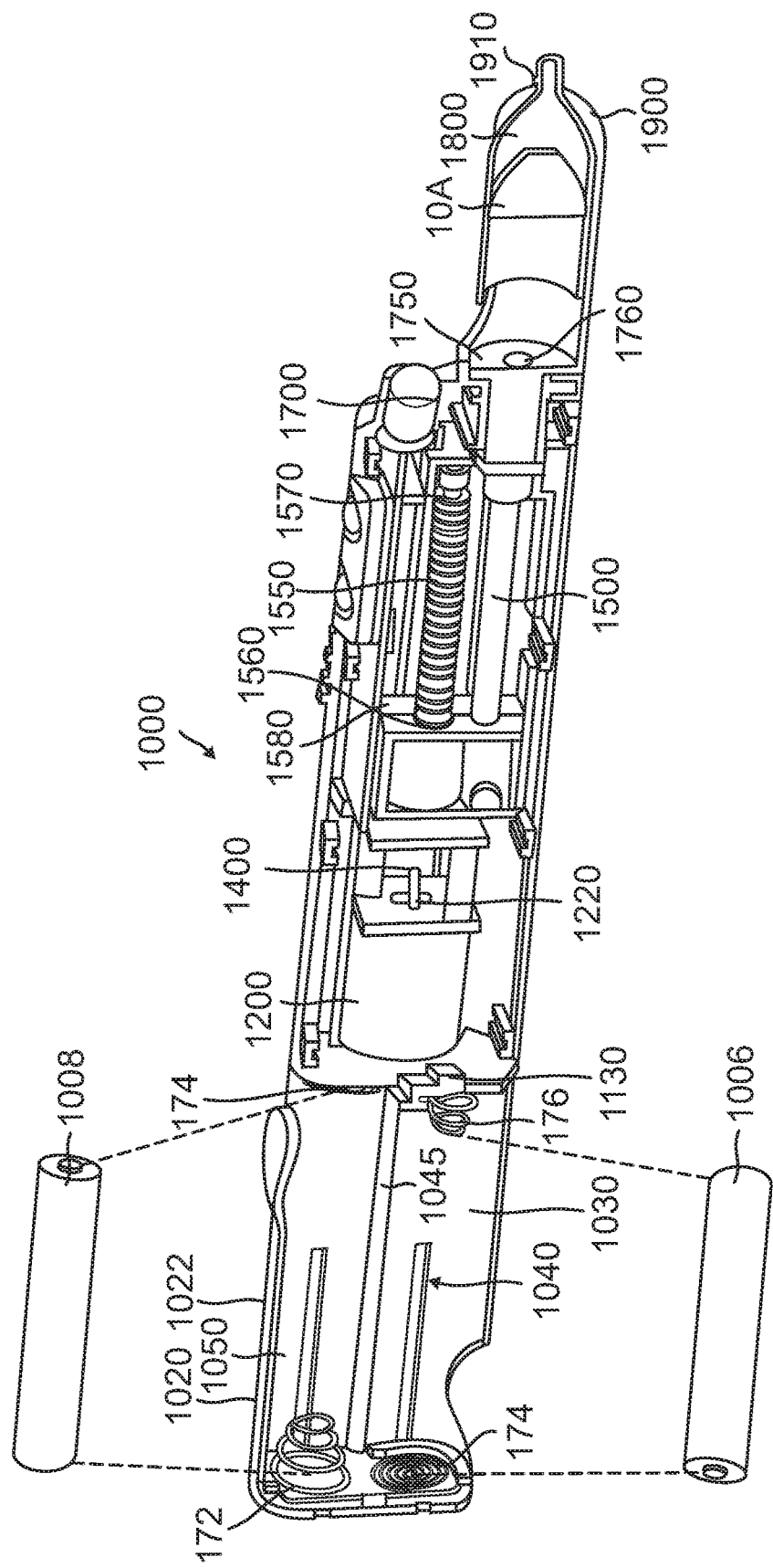
FIG. 1 is a side cross-sectional view of the dispensing pen which retains a single use cartridge within the dispensing pen and further discloses the present invention electrical motor mechanism connected to a gear mechanism which in turn is connected to a movement shaft having a multiplicity of teeth along the length of the movement shaft which interacts with mating teeth on a connector block which in turn is connected at a rear of an advancing shaft so that as the gear mechanism causes the movement shaft to move in a certain direction, the teeth of the movement shaft engage with the teeth of the connecting block and move the advancing shaft incrementally forward, which advancing shaft and movement shaft are shown in the starting position in FIG. 1 and a single use cartridge is illustrated with a sealing plunger, a first pushbutton switch, a second pushbutton switch, a programmable PCB board and a battery compartment at the rear of the dispensing pen, also disclosed is an exploded view of two batteries which are inserted into the battery compartment, which batteries are separated by a dividing wall.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The variations on the single use cartridges have been summarized in detail in the summary of the invention section. The cartridge variations are summarized as follows:

(1) a single use cartridge having a single interior chamber housing a compound. This variations has two sub-variations: (a) the single use cartridge is within a chamber within the electrical dispensing pen with a nozzle extending out of an opening in the dispensing pen; and (b) the single use cartridge is threaded onto threads adjacent the opening of the electrical dispensing pen and is outside of the dispensing pen. In both sub-variations, the nozzle from the single use cartridge is threaded onto an applicator or brush.

(2) A single use cartridge having a double interior chamber divided by a dividing wall so that a respective compound is in each separate chamber of the dual chamber single use cartridge. This variations also has the same two sub-variations: (a) the single use cartridge is within a chamber within the electrical dispensing pen with a nozzle extending out of an opening in the electrical dispensing pen; and (b) the single use cartridge is threaded onto threads adjacent the opening of the dispensing pen and is outside of the dispensing pen. In both sub-variations, the nozzle from the single use cartridge is threaded onto a mixing chamber where the two compounds are mixed after being dispensed from the single use cartridge, and the mixing chamber has a nozzle which is threaded onto an applicator or brush after the mixing process. These variations and sub-variations will be described after discussion of the new innovations in this invention.

The variations are all utilized with the electrical motor mechanism for advancing an advancing shaft with a piston within the dispensing pen to push against a pocket in a sealing plunger located adjacent the interior rear of the single use cartridge. For the variation where the single use cartridge has one chamber, the sealing pushing plunger has one pocket to receive one pushing piston. For the variation where the single use cartridge has a dual chamber, the sealing pushing plunger has two pockets to respectively receive a respective one of the dual pushing pistons to push a respective half of a the sealing plunger to dispense each respective compound. In either variation, the electrical motor mechanism is connected to a gear mechanism which in turn rotates the movement shaft which in turn causes the advancing shaft to respectively push a single plunger in a single chamber cartridge or dual plungers in a dual chamber cartridge.

The dispensing pen has two variations. In one variation the dispensing pen has an interior chamber to receive the single use cartridge within the dispensing pen. This variation will be described first. FIG. 1, FIG. 2, FIG. 3 and FIG. 4 show alternative conditions of this variation. Referring to FIG. 1, FIG. 2, FIG. 3 and FIG. 4, FIG. 1, FIG. 3 and FIG. 4 are cross-sectional views and FIG. 2 is a partial cross-sectional view, There is illustrated the electric motor 1200 connected to a gear mechanism 1400 which rotates the movement shaft 1550.

Figure 2:
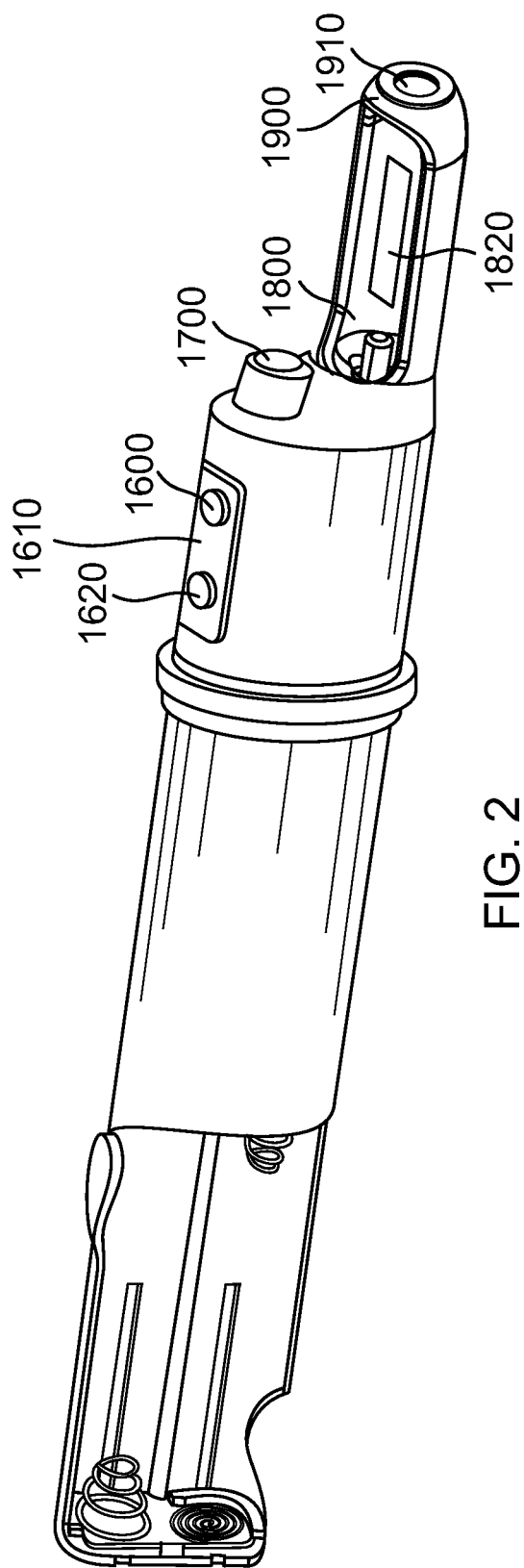
FIG. 2 is a top left partial side cross-sectional view of the dispensing pen of FIG. 1, illustrating an anti-rotation member within the chamber into which the single use cartridge is inserted, the battery compartment, the first push button switch, the second push button switch, a programmable printed circuit board and the light.

Referring to FIGS. 1 through 4, the dispensing pen 1000 has a circumferential wall 1020 with an exterior surface 1022 and an interior surface 1030. The dispensing pen 1000 has a rear interior chamber 1050 surrounded by a portion of interior surface 1030. The rear interior chamber 1040 houses a battery compartment 1050 which as illustrated has a first positive pole 170 and first negative pole 172 and a second negative pole 176 and second positive pole 174. As illustrated in FIG. 1, a first battery 1006 is retained between first positive pole 170 and first negative pole 172. A second battery 1008 is retained between second positive pole 176 and second negative pole 174. A dividing wall 1045 separates the batteries. The battery poles are electrically connected by an electrical connector member 1130 to an electric motor 1200.

Referring to FIG. 1, the electric motor 1200 is preferably a DC motor run by batteries which can be standard batteries 1006 and 1008 such as "AA" or rechargeable batteries. It is also within the spirit and scope of the present invention for a power unit to replace the batteries with the power unit connected to a transformer connected to a source of alternating current, the transformer reducing the voltage and converting it to direct current. The electric motor 1200 is of conventional design and includes a rotating shaft 1220 which is connected to a gear assembly 1400. The gear assembly 1400 is connected at one end to the rotating shaft 1220 of the electric motor 1200 and connected at the opposite end to the movement shaft 1550. Referring to FIG. 1, the gear box assembly 1400 has a first set of gears connected at one end to the rotating shaft 1220 of the electric motor 1200 and connected at the opposite end of the gear box assembly to a movement shaft 1550. The movement shaft 1550 has a rear or proximal end 1560 connected to the gear assembly 1400 and has a front or distal end 1570. The electric motor 1200 is connected to a programmable printed circuit board 1610 which is connected to a first activation member such as first pushbutton 1600 and to a second activation member which is second pushbutton 1620.

Figure 3:
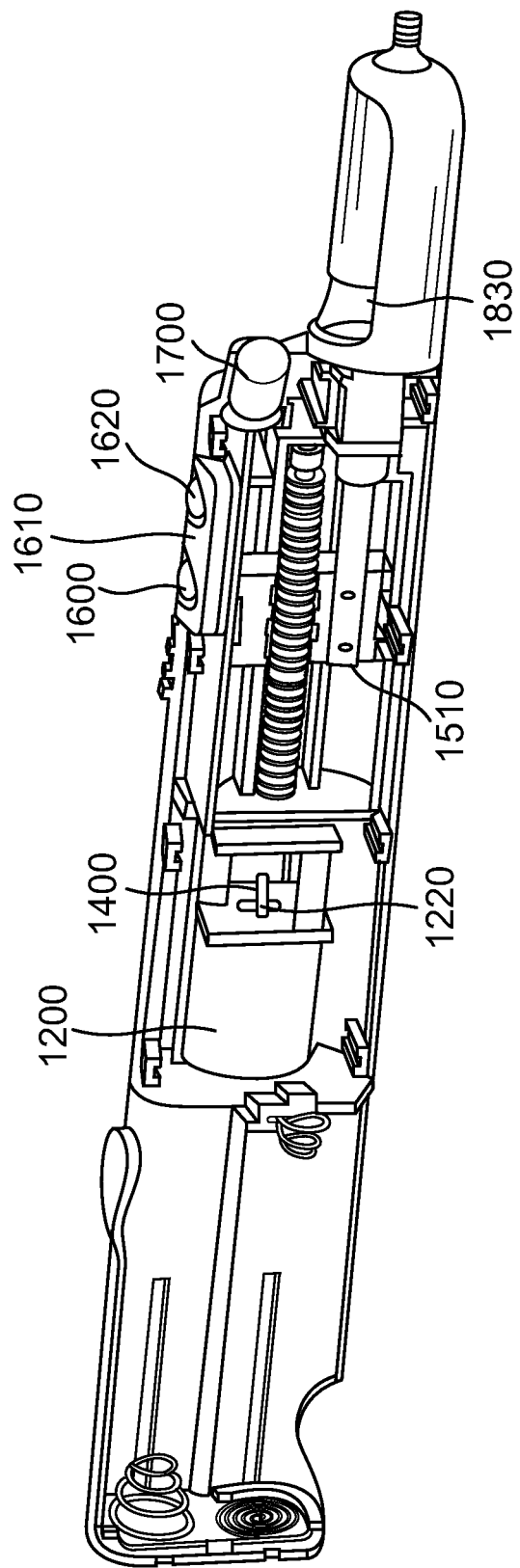
FIG. 3 is a side cross-sectional view of the dispensing pen which retains a single use cartridge within the dispensing pen and further discloses the present invention electrical motor mechanism connected to a gear mechanism which in turn is connected to a movement shaft having a multiplicity of teeth along the length of the movement shaft which interacts with mating teeth on a connector block which in turn is connected at a rear of an advancing shaft so that as the gear mechanism causes the movement shaft to move in a certain direction, the teeth of the movement shaft engage with the teeth of the connecting block and move the advancing shaft incrementally forward, which advancing shaft and movement shaft are shown in a partially moved condition in FIG. 3 and a single use cartridge is illustrated with a sealing plunger, a first pushbutton switch, a second pushbutton switch, a programmable PCB board and a battery compartment at the rear of the dispensing pen, with the illustration of the connecting block now advanced to the center location and the advancing shaft moved partially into the single use cartridge.
Figure 4:
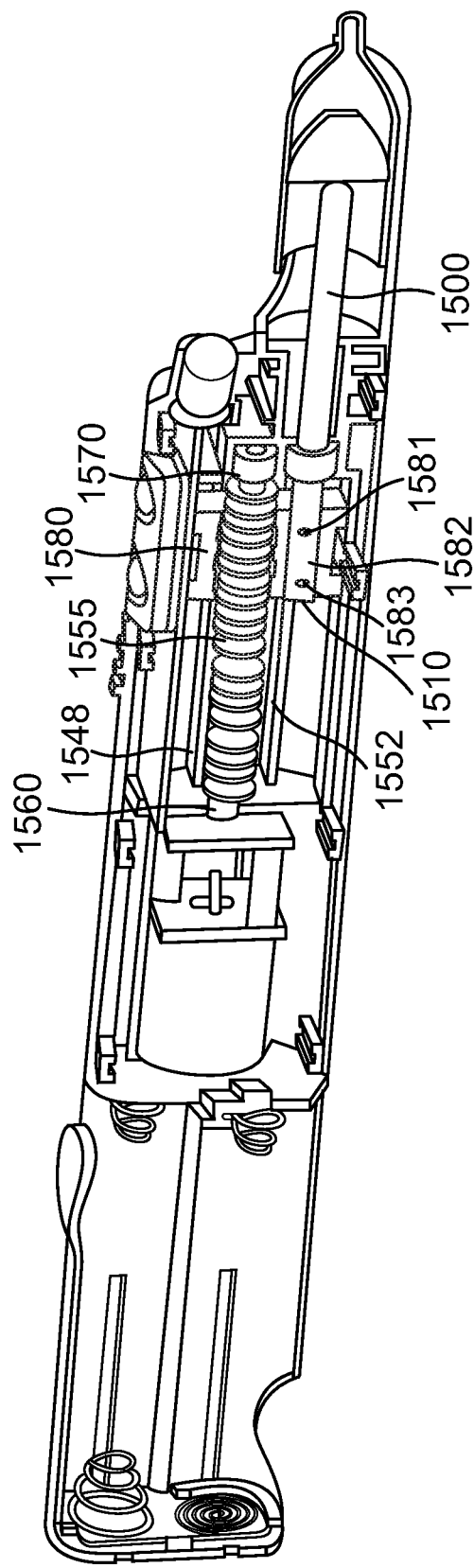
FIG. 4 is a side cross-sectional view of the dispensing pen which retains a single use cartridge within the dispensing pen and further discloses the present invention electrical motor mechanism connected to a gear mechanism which in turn is connected to a movement shaft having a multiplicity of teeth along the length of the movement shaft which interacts with mating teeth on a connector block which in turn is connected at a rear of an advancing shaft so that as the gear mechanism causes the movement shaft to move in a certain direction, the teeth of the movement shaft engage with the teeth of the connecting block and move the advancing shaft incrementally forward, which advancing shaft and movement shaft are shown in the final advanced position in FIG. 4 and a single use cartridge is illustrated with a sealing plunger, a first pushbutton switch, a second pushbutton switch, a programmable PCB board and a battery compartment at the rear of the dispensing pen, with the movement shaft now in its fully extended condition, the movement block in its fully extended condition and the advancing shaft penetrating through the plunger of the single use cartridge to dispense compounds from the single use cartridge.
Figure 4A:
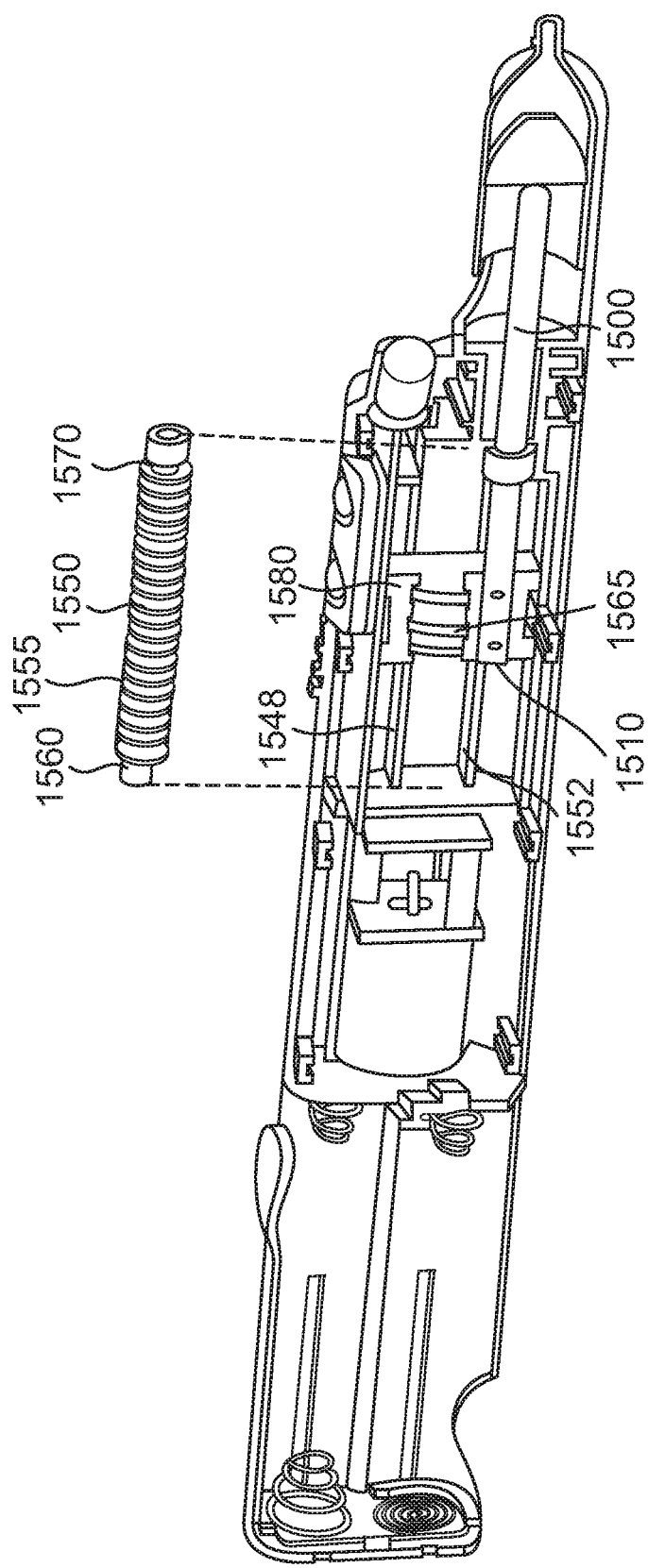
FIG. 4A is a side cross-sectional view of the dispensing pen which retains a single use cartridge within the dispensing pen and further discloses the present invention electrical motor mechanism connected to a gear mechanism which in turn is connected to a movement shaft having a multiplicity of teeth along the length of the movement shaft which interacts with mating teeth on a connector block which in turn is connected at a rear of an advancing shaft so that as the gear mechanism causes the movement shaft to move in a certain direction, the teeth of the movement shaft engage with the teeth of the connecting block and move the advancing shaft incrementally forward, which advancing shaft and movement shaft are shown in the partially moved condition and a single use cartridge is illustrated with a sealing plunger, a first pushbutton switch, a second pushbutton switch, a programmable PCB board and a battery compartment at the rear of the dispensing pen, with the illustration of the connecting block now advanced to the center location and the advancing shaft moved partially into the single use cartridge, with the movement shaft removed from the connecting block to disclose the engaging teeth in the connecting block.

The description of the dispensing pen in FIGS. 1, 2, 3, 4 and 4A have been described in detail in the Brief Description of the Drawings section. The difference in the figures is that it illustrates the operating mechanism in different conditions. As described, in FIG. 1 the operating mechanism is in its initial condition where the movement shaft 1550 has not yet moved and the connecting block 1580 has also not moved. As illustrated in FIG. 4A, the connecting block 1580 has connecting teeth 1565 which engage with the teeth 1555 on the movement shaft 1550. The connecting block is connected at its lower end by affixation means such as rivets 1583 and 1581 to a connecting end section 1582 of the advancing shaft 1500 having a proximal end 1510. The connected block 1580 also slides along interior shelves 1548 and 1552.

A pre-programmable printed circuit board 1610 is used so that when either activation mechanism 1600 or 1620 are activated or pushed through pushbuttons, a circuit is closed and the pre-programmable printed circuit board 1610 causes the electric motor 1200 to start. The gears in the gear assembly 1400 rotate in a given direction which causes the movement shaft 1550 to move in a circular direction where the teeth 1555 engage the teeth 1565 of the connecting block causing the connecting block to move forwardly toward the front of the dispensing pen. With the connecting block attached to the rear of the advancing shaft 1500, the advancing shaft is also caused to move toward the front of the dispensing pen.

In FIG. 3, the operating mechanism has been activated so that the connecting block 1580 has now moved to the center of the interior chamber and the advancing shaft 1500 has now been moved so that it is partially penetrating into the interior chamber 1800 which retains the single use cartridge 10A. In FIG. 4, the cycle has been completed where the movement shaft has been rotated a sufficient amount so that the connecting block 1580 has now moved to adjacent the distal end 1570 of the movement shaft 1550. The advancing shaft 1500 is now shown having been penetrating through the single use cartridge and is pushing a plunger in the single use cartridge as will be discussed. When the second activation mechanism 1620 is activated, the movement shaft 1550 is caused to rotate in the opposite direction, thereby causing the teeth 1555 to engage the connecting block teeth 1565 to move the connecting block 1580 toward the rear of the dispensing pen, thereby causing the advancing shaft 1500 to move toward its starting position and be concluded in its starting position.

With the pre-programmable printed board 1610, the movement can be incremental so that compound is pushed out slowly from the unidose cartridge and return of the advancing shaft to its initial condition can also be through incremental movements.

Also illustrated is a light 1700 which provides a source of illumination to enable the dispensing of compound into a person's mouth or other locations to be more clearly visible. The source of illumination 1700 is lit when either of the activation members 1600 or 1620 are activated. The dispensing pen has an interior chamber 1800 which receives the unidose cartridge 10A and has an opening 1910 through which a nozzle of the unidose cartridge is inserted as will be described.

Figure 5:
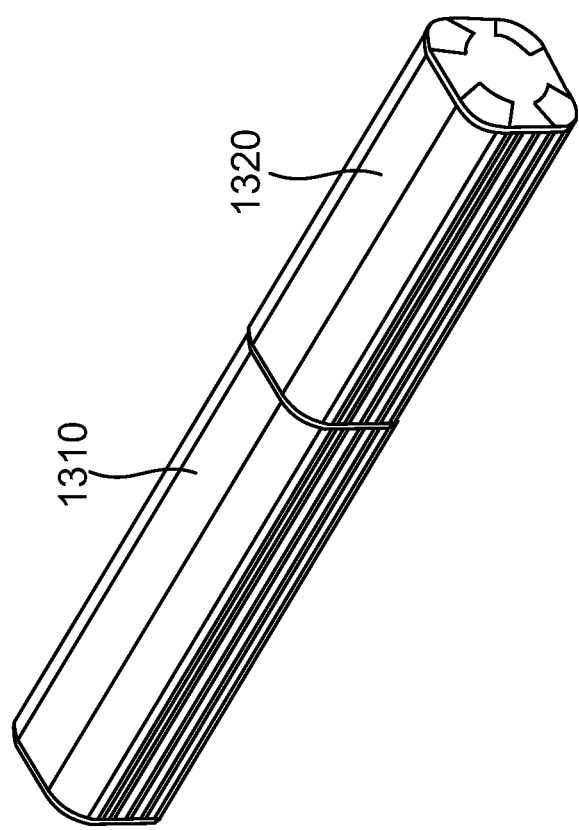
FIG. 5 is a top perspective view of the enclosed dispensing pen with a first section of the cover covering the battery compartment, motor and gear assembly and the second portion of the cover covering the pushbutton activation switch, the printed circuit boards, the movement shaft, the advancing shaft, the connecting block and the chamber retaining a single use cartridge with a dispensing applicator connected to the tip of the dispensing cartridge.

In a first and preferred embodiment of the dispensing pen 1000, a cartridge retaining interior chamber 1800 is located between an interior dividing wall 1750 and the front 1900 of dispensing pen 1000. The cartridge retaining interior chamber 1800 is surrounded by a portion of interior surface 1030 and exterior wall 1020. As illustrated in FIG. 5, the cover is a two-part cover 1310 and 1320. When the second cover part 1320 is removed, it exposes the cartridge retaining interior chamber 1800 into which a unidose cartridge is inserted, as illustrated in FIG. 3 and as will be explained in detail later on. The interior dividing wall 1750 separates the advancing shaft 1500 and the movement shaft 1550 from the cartridge retaining interior chamber 1800. The interior dividing wall 1750 includes an opening 1760 through which the advancing shaft 1500 passes. The front 1900 includes an opening 1910 through which a nozzle of a cartridge passes. An anti-rotation member 1820 extends from a portion of the interior surface 1030 at the cartridge retaining interior chamber 1800 and extends into the chamber 1800. When the cartridge is inserted, the anti-rotation member 1820 extends into an anti-rotation receiving member in the cartridge as will be described to prevent the cartridge from rotating within the dispensing pen.

FIG. 5 is a top perspective view of the enclosed dispensing pen with a first section 1310 of the cover covering the battery compartment, motor and gear assembly and the second section 1320 of the cover covering the pushbutton activation switch, the printed circuit boards, the movement shaft, the advancing shaft, the connecting block and the chamber retaining a single use cartridge with a dispensing applicator connected to the tip of the dispensing cartridge.

Figure 5A:
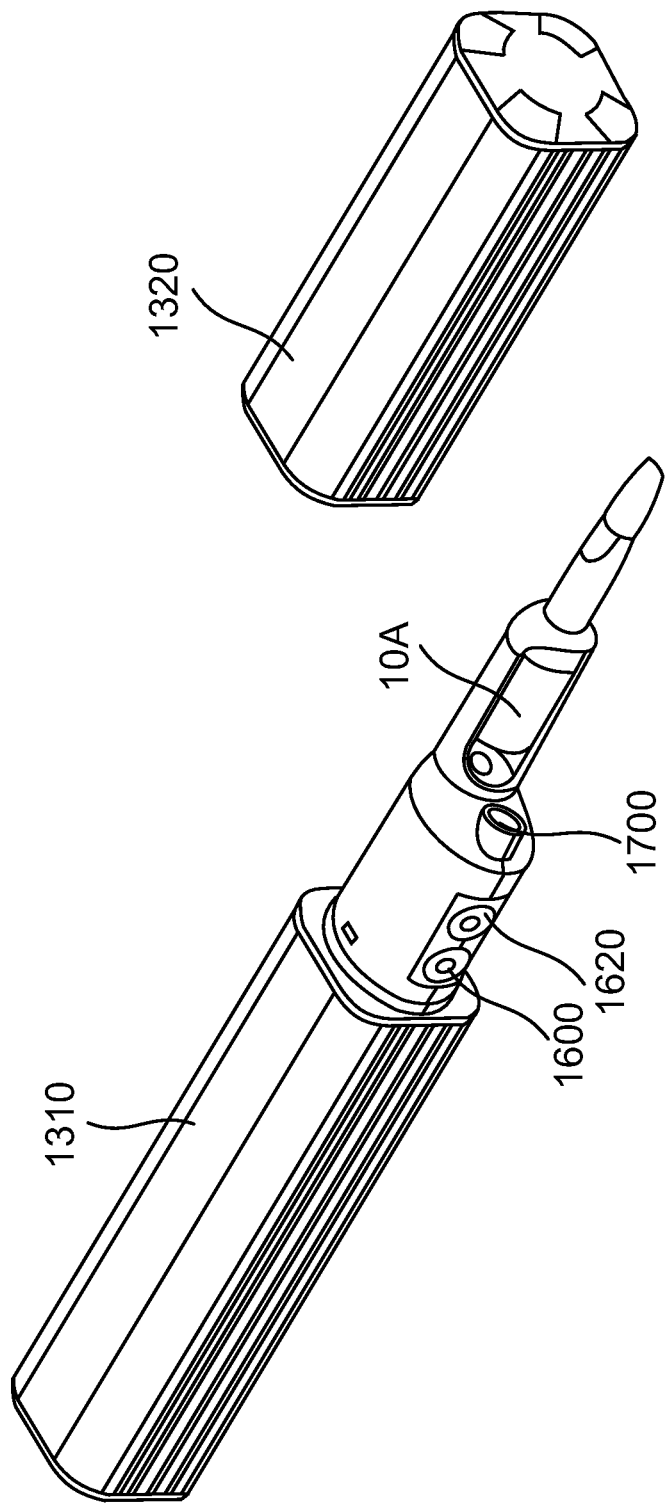
FIG. 5A is a top left side exterior perspective view of the present invention dispensing pen with the first section of the cover in place covering the battery compartment, the electrical motor and the gear assembly and the second portion of the cover removed to illustrate the exterior portion of the dispensing pen including the pushbutton activation switches and the printed circuit board with the movement shaft, the advancing shaft and the connecting block concealed but exposing the interior open chamber retaining a single use cartridge which is affixed to an applicator, the second cover being shown moved from the assembly to illustrate the front portion of the dispensing pen.

FIG. 5A is a top left side exterior perspective view of the present invention dispensing pen with the first section 1310 of the cover in place covering the battery compartment, the electrical motor and the gear assembly and the second section 1320 of the cover removed to illustrate the exterior portion of the dispensing pen including the pushbutton activation switches and the printed circuit board with the movement shaft, the advancing shaft and the connecting block concealed but exposing the interior open chamber retaining a single use cartridge which is affixed to an applicator, the second cover being shown moved from the assembly to illustrate the front portion of the dispensing pen.

Figure 5B:
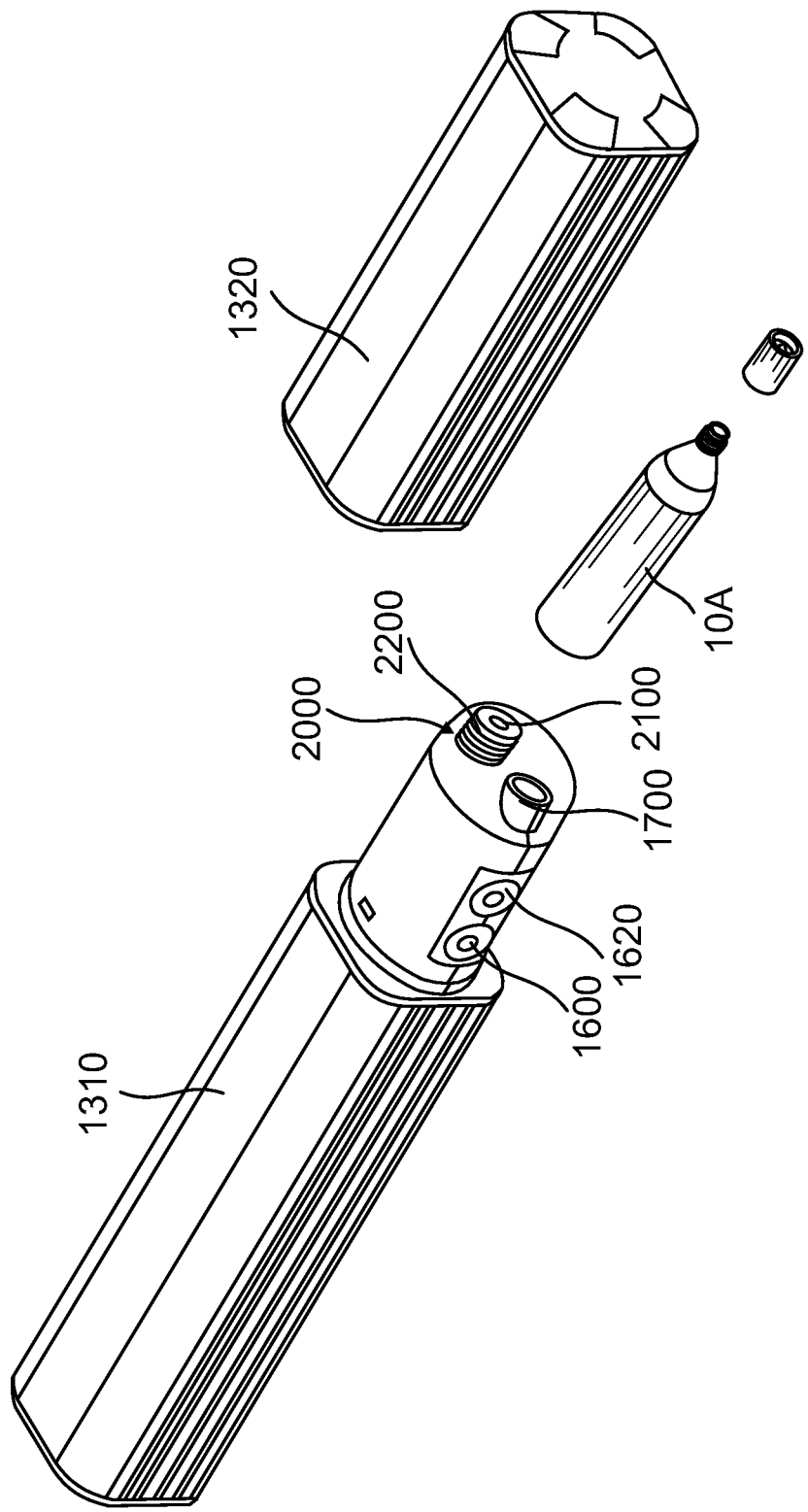
FIG. 5B is a perspective view of an alternative embodiment of the present invention where the single use cartridge is retained on the front of the dispensing pen, the view in FIG. 5 illustrating the attaching mechanism on the front of the dispensing pen with an opening which receives the advancing shaft and the single use cartridge shown in exploded condition away from the attaching mechanism, with the second portion of the cover also shown removed.

FIG. 5B is a perspective view of an alternative embodiment of the present invention where the single use cartridge is retained on the front of the dispensing pen, the view in FIG. 5B illustrating the attaching mechanism 2000 on the front of the dispensing pen with an opening 2100 which receives the advancing shaft and the single use cartridge shown in an exploded condition away from the attaching mechanism, with the second portion 1320 of the cover also shown removed.

Figure 5C:
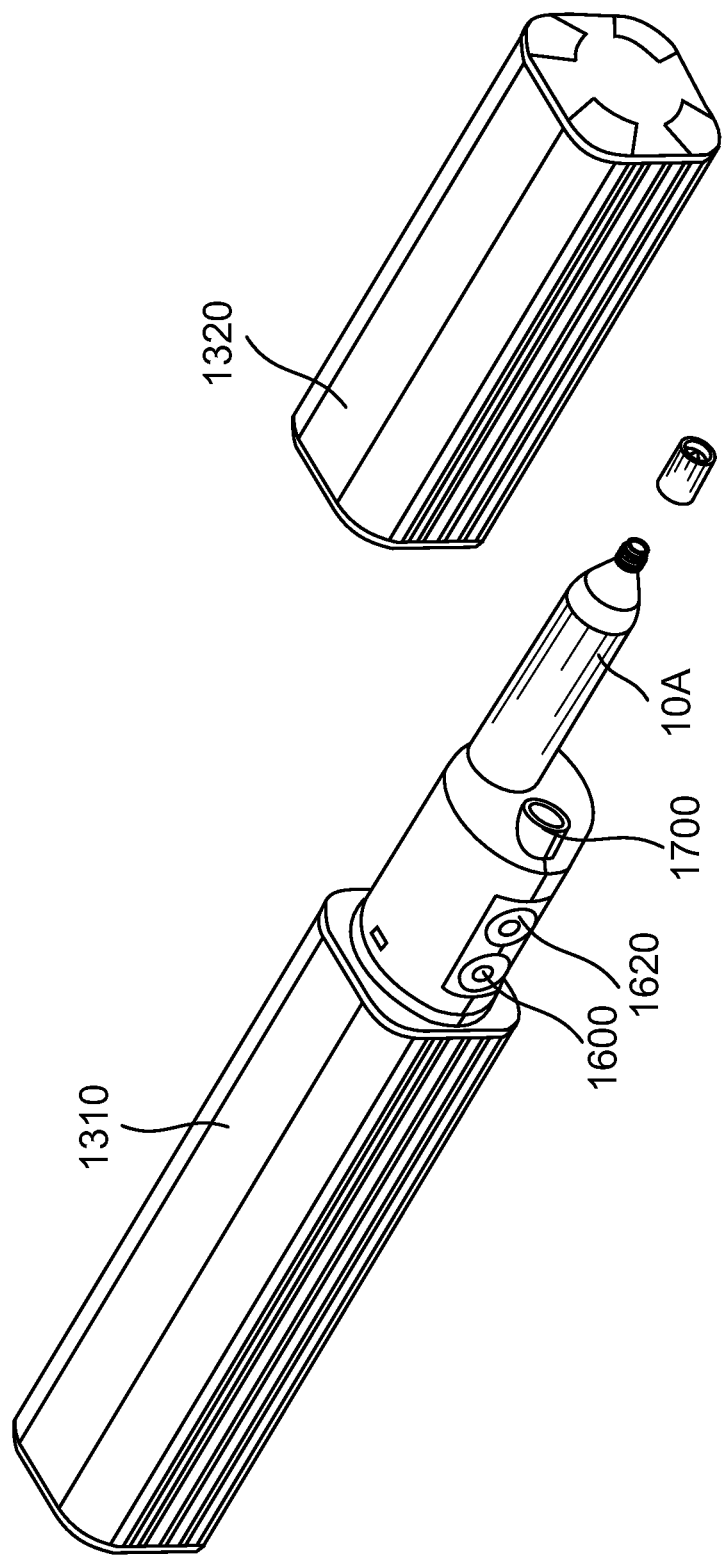
FIG. 5C is a perspective view of the alternative embodiment of the present invention where the single use cartridge is now affixed onto the front of the dispensing pen with the front cap removed to illustrate this feature of the alternative embodiment of the present invention.

FIG. 5C is a perspective view of the alternative embodiment of the present invention where the single use cartridge is now affixed onto the front of the dispensing pen with the front cap removed to illustrate this feature of the alternative embodiment of the present invention.

Figure 6:
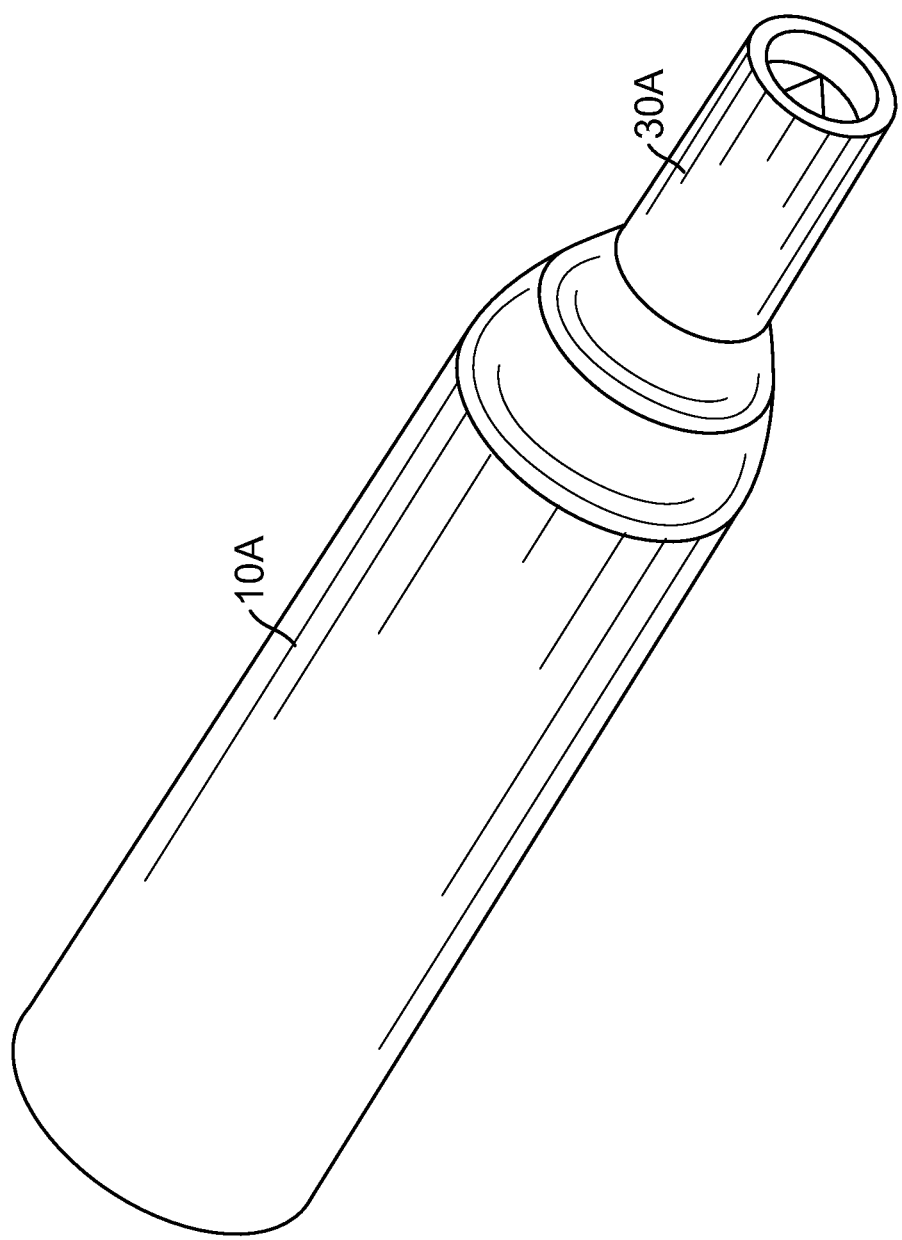
FIG. 6 is a top perspective view of the unidose single use cartridge which contains a compound as defined above including compound selected from the group consisting of a tooth whitening compound, a dental bonding and filling compound, a nail polish, and an adhesive compound in a sealed condition with the cap threadedly retained onto the single use cartridge, and which cartridge is disposed of and replaced with a new single use cartridge for subsequent application of a compound.

Referring to FIG. 6, there is illustrated an exterior perspective view of a cartridge or cartridge 10A with a front cap 30A attached, which is used when the cartridge is inserted into the interior chamber 1800 within the dispensing pen 1000. The interior of the cartridge will vary as discussed above. For a single interior chamber cartridge, the letter "A" is used with a corresponding part. The letter "A" is not used when the interior of the cartridge 10 has a dual chamber. The exterior is the same for both. In FIGS. 6, 7, 8 and 9, the letter "A" is used since the cross-sectional view of FIG. 9 illustrates a cartridge 10A with a single interior chamber.

Figure 7:
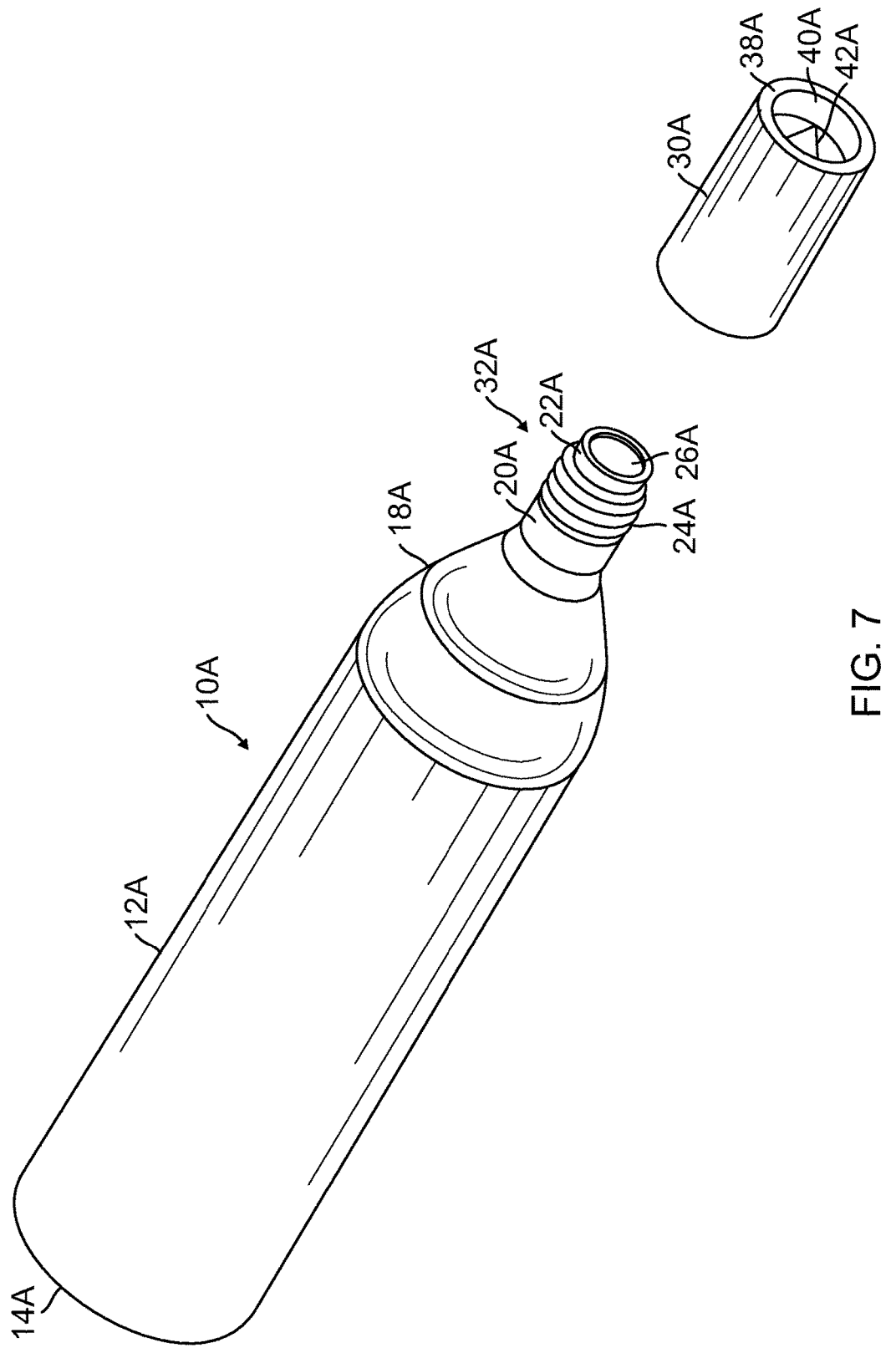
FIG. 7 is an exploded view showing the same cartridge illustrated in FIG. 6 but with the sealing cap removed, the single use cartridge having an exterior surface which is generally cylindrical in shape and a rear surface which is generally flat with an opening, a front surface which is generally frustum shaped extending from the body of the cylinder to a nozzle having a cylindrical surface extending from the frustum and extending to a dispensing nozzle tip having threads on the exterior surface and a frangible seal on the front end of the tip, also illustrating the threaded cap which is cylindrical and a front end with an interior chamber having a piercing tooth.

Further referring to FIG. 7, there is illustrated an exploded exterior view of a single use cartridge 10A with the cap 30A unscrewed. The single interior use cartridge 10A contains an exterior surface 12A which is generally cylindrical in shape and a rear surface 14A which is generally flat. The front surface 18A is generally frustum shaped extending from the body of the cylinder 10A to a nozzle 32A having a cylindrical surface 20A extending from the frustum 18A and extending to a dispensing nozzle tip 22A having threads 24A on the exterior surface and a frangible seal 26A on the front end of the tip 22A. The threaded cap 30A is cylindrical with a front end 38A with an interior chamber 40A having a piercing tooth 42A within the interior 40A which extends inwardly from the front end 38A of the sealing cap 30A. In use, after the cartridge 10A is placed in the dispensing pen 1000 as will be discussed, the front or tip 22A of the single use cartridge 10A extends through an opening in the dispensing pen and the threaded cap 30A which is previously unscrewed from the threads 24A of the cartridge 30A before the cartridge 10A is inserted into the dispensing pen 1000, is then rotated 180 degrees so that the sharp tooth 42A penetrates the frangible seal 26A so that the tip 22A is opened and a selected compound 100A is dispensed from the interior 50A of the cartridge 10A.

Figure 8:
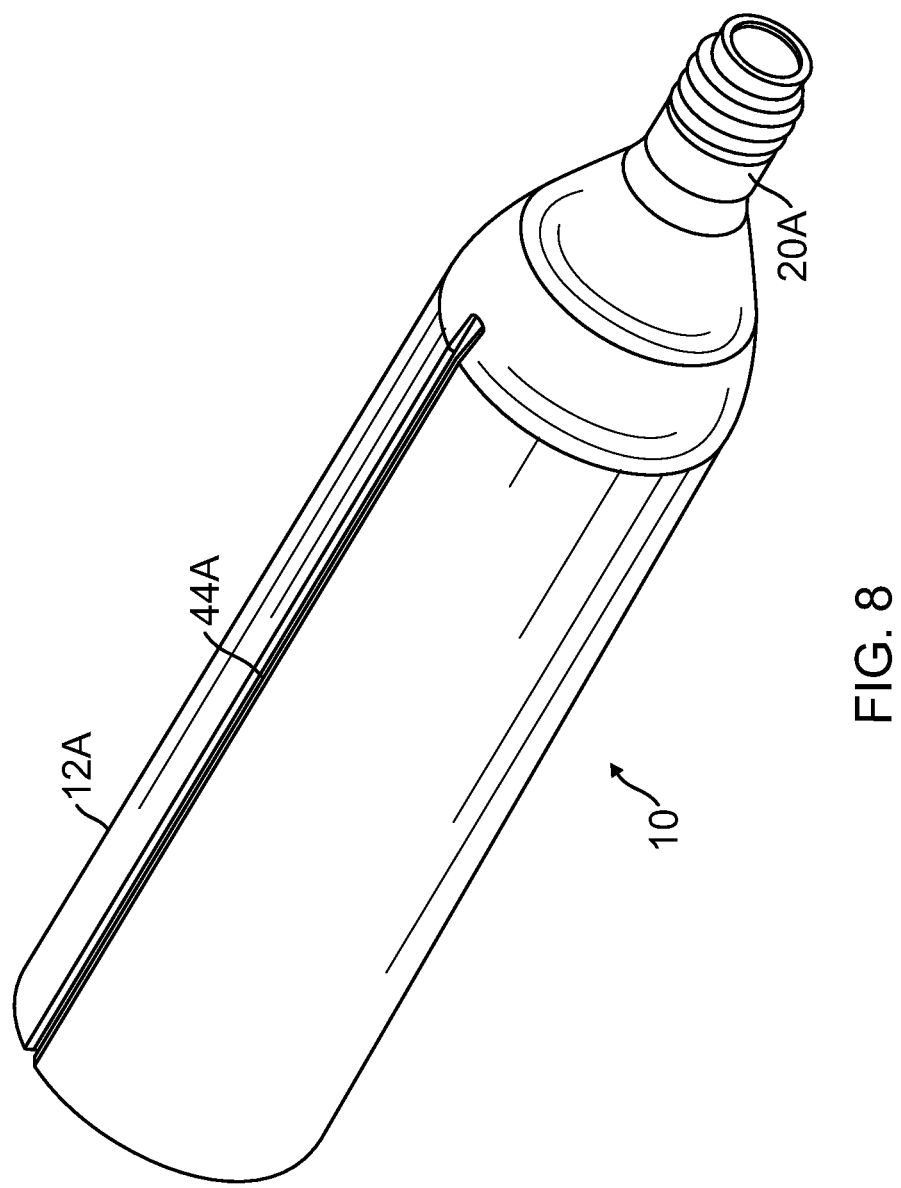
FIG. 8 is a bottom perspective view of the unidose single use cartridge with an anti-rotation slit in the bottom of exterior surface of the exterior wall of the single use cartridge, the slit does not extend so deep that it goes into the interior chamber of the cartridge, the purpose of the anti-rotation slit is to be inserted into a mating member in the dispensing pen to prevent the cartridge from rotating once it is placed into the pen.
Figure 9:
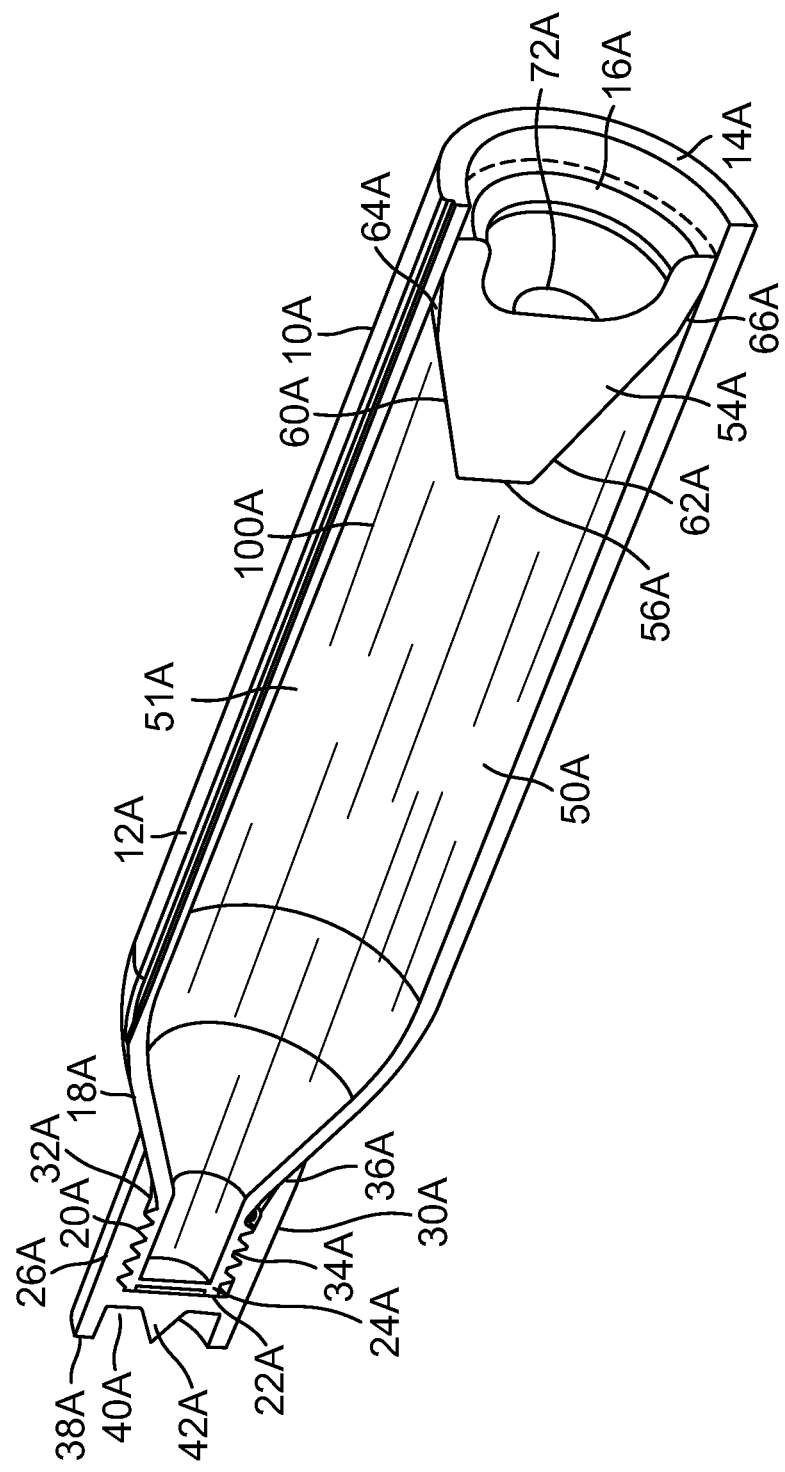
FIG. 9 is a side cross-sectional view of a first embodiment of the unidose single use cartridge illustrating a single interior chamber which retains one compound, and a rear plunger having an interior face to push the compound in the interior of the cartridge forward and out of the cartridge, and an angular sidewall ending in a rear wall forming a seal against the interior sidewall, the rear end of the plunger having a pocket to receive a single pushing piston.

Referring to FIG. 8, there is a illustrated bottom perspective view of the unidose single use cartridge 10A. The difference between the top view and the bottom view is that bottom view shows an anti-rotation slit 44A in the bottom of exterior surface 12A. The slit 44A does not extend so deep that it goes into the interior chamber as will be discussed. The purpose of the anti-rotation slit 44A is to be inserted into a mating member anti-rotation member 1820 in the cartridge retaining interior chamber 1800 of the dispensing pen 1000 to prevent the cartridge 10A from rotating once it is placed into the cartridge retaining interior chamber 1800 of the dispensing pen 1000.

Referring to FIG. 9, there is illustrated a side cross-sectional view of a first embodiment of the unidose single use cartridge with sealing cap affixed, illustrating a single interior chamber which retains one compound, and a rear plunger having an interior face to push the compound in the interior of the cartridge forward and out of the cartridge, and an angular sidewall ending in a rear wall forming a seal against the interior sidewall, the rear end of the plunger having a pocket to receive a single pushing piston. The cartridge 10A has a single interior chamber 50A with a single compound 100A retained in the interior chamber 50A. A rear plunger 54A having an interior face 56A is used to push the compound 100A in the interior chamber 50A forward and out of the cartridge 10A. The rear plunger 54A has a pair of opposed rear angular sides 60A and 62A extending from opposite ends of the interior face 56A and respectively ending in rear sidewalls 64A and 66A forming a seal against the interior sidewall 51A of the cartridge 10A, the interior of each rear sidewall 64A and 66A of the plunger 54A forming the sidewalls of a pocket 72A to receive the pushing piston from the dispensing pen.

Figure 10:
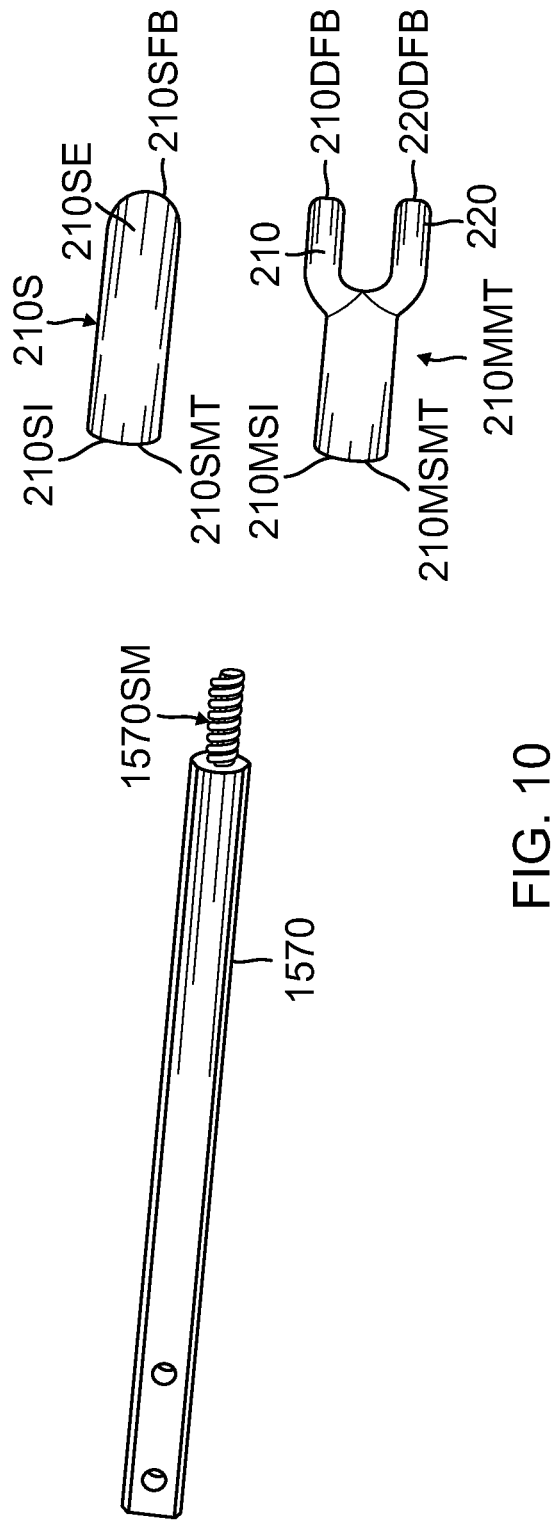
FIG. 10 is an exploded view illustrating the front of the advancing shaft of the present invention and a single piston and a dual piston.

Further referring to FIG. 9, the single use cartridge with the single interior chamber 51A contains an exterior surface 12A which is generally cylindrical in shape and a rear surface 14A which is generally flat with an opening 16A through which a pushing piston 210S is inserted into pocket 72A, a front surface 18A which is generally frustum shaped extending from the body of the cylinder 10A to a nozzle 32A having a cylindrical surface 20A extending from the frustum 18A and extending to a dispensing nozzle tip 22A having threads 24A on the exterior surface and a frangible seal 26A on the front end of the tip 22A. A threaded cap 30A is cylindrical with an interior surface 32A with threads 34A adjacent the rear 36A of the sealing cap 30A and a front end 38A with an interior chamber 40A having a piercing tooth 42A within the interior 40A which extends inwardly from the front end 38A of the sealing cap 30A. In use, after the cartridge 10A is placed in the dispensing pen 1000 as will be discussed, the front or tip 22A of the single use cartridge 10A extends through the opening 1910 in the front 1900 of the dispensing pen 1000 and the threaded cap 30A which is previously unscrewed from the threads 24A of the cartridge 30A before the cartridge 10A is inserted into the dispensing pen 1000, and is then rotated 180 degrees so that the sharp tooth 42A penetrates the frangible seal 26A so that the tip 22A is opened and a selected compound 100A is dispensed from the interior 50A of the cartridge 10A Referring to FIG. 10, there is illustrated the two types of pushing pistons attached to the front 1570 of the advancing shaft 1500 described in detailed when discussing FIGS. 1 through 4. The front 1570 of the advancing shaft 1500 has a first mating member 1570SM which in an illustrative embodiment has male threads. There is a single piston 210S with a shaft second mating portion. 210SMT. For the illustrative embodiment where the first mating member 1570SM of the multi-sectional shaft 1570 has male threads, the shaft second mating portion 210SMT has mating female threads 210SI within the single piston. In an embodiment, the single pushing piston 210S has a cylindrical exterior 210SE with a rounded bullet shaped front 210SFB which is inserted into pocket 72A in the interior of single chamber cartridge 10A. The single pushing piston 210S has a partially hollow interior which would have the female mating threads. For a cartridge 10 having a dual chamber, the pushing piston 210 has a mating section 210MMT which branches into a first piston 210 and a spaced apart second piston 220. For the illustrative embodiment where the first mating member 1570SM of the multi-sectional shaft 1570 has male threads, the mating section 210MMT shaft second mating portion 210MSI has a partially hollow interior which would have mating female threads within its interior 210MSI. In an embodiment, the mating section 210MMT has a cylindrical exterior which branches into first piston 210 having a bullet shaped front 210DFB and a second piston 220 with a bullet shaped front 220DFB which are respectively inserted in pushing plunger pockets as will be described.

FIG. 4 illustrates a cross-sectional view where a pushing piston 210S is placed onto the front end 1570 of the advancing shaft 1500. As illustrated in FIG. 3, in one variation, the single use cartridge 10A is placed within the cartridge receiving interior opening adjacent to front 1900 of the dispensing pen 1000 with the threaded nozzle 12A extending through the opening 1910 in the front 1900 of the dispensing pen 1000. For the single chamber cartridge 10A illustrated in FIG. 7, the single piston mating section 210S is affixed to the front of the advancing shaft 1500 and the single pushing piston 210S is guided into the rear pocket 72A. For the dual chamber cartridge 10 illustrated in FIG. 11, the mating section 210MMT is affixed to the front of the advancing shaft 1500 and a respective one of the dual pushing pistons 210 and 220 is guided into a respective pocket 72 and 74.

Figure 11:
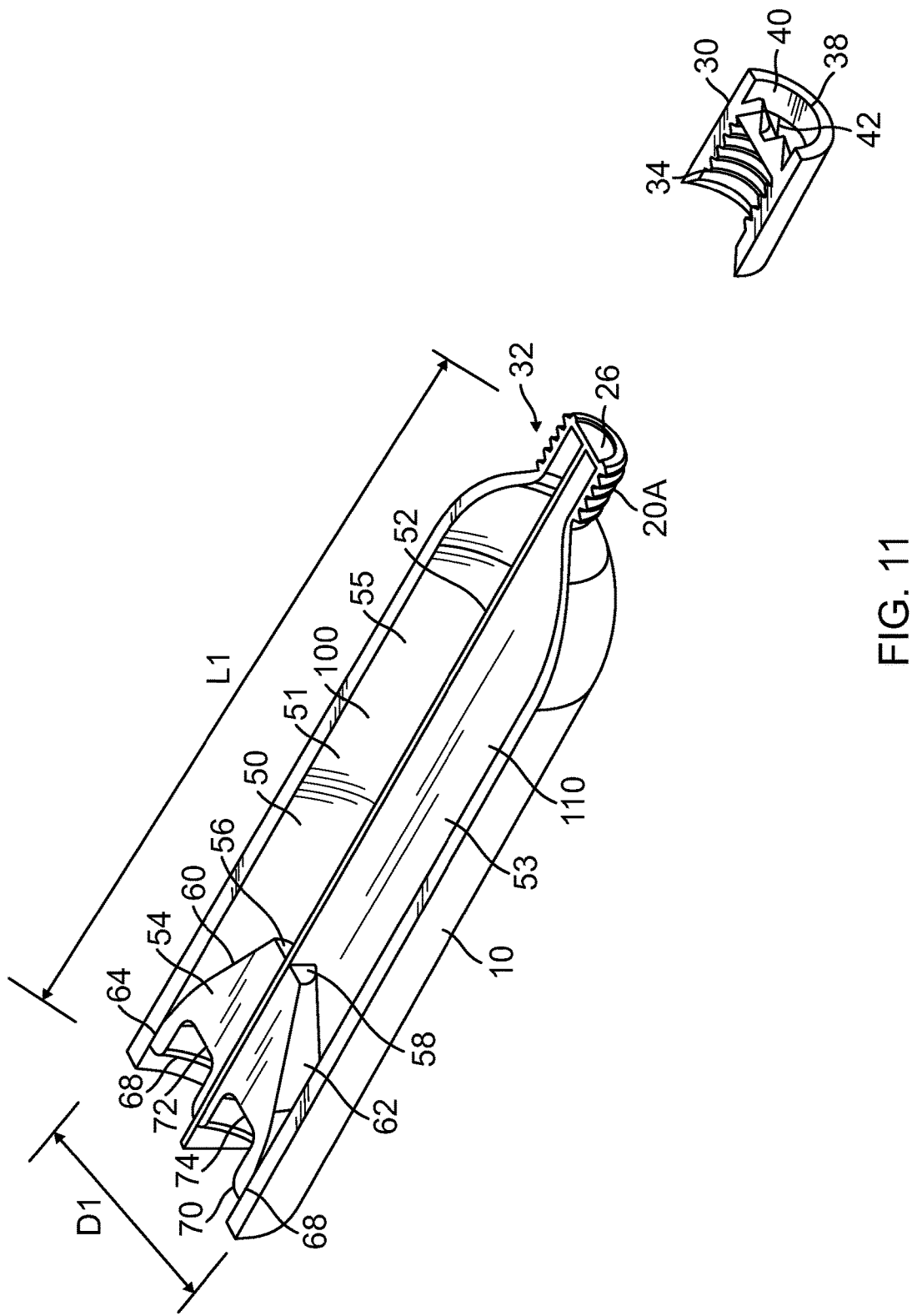
FIG. 11 is a top cutaway view of a second embodiment of the unidose single use cartridge having a divided interior chamber which retains two separate compounds which are separated from each other while in the cartridge by a dividing wall, and a rear plunger having opposing interior faces to push a compound in a respective portion of the interior of the cartridge forward and out of the cartridge, and a pair of opposed angular sidewalls ending in rear wall sidewalls forming a seal against the interior sidewall of the cartridge, each rear end of the plunger having a pocket to receive a respective pushing piston from the dispensing pen.

Referring to FIG. 11, the alternative cartridge 10 with a dual chamber interior is illustrated in a top cutaway view of the second embodiment of the unidose single use cartridge 10 containing the divided interior chamber 50 which retains two separate compounds 100 and 110 which are separated from each other while in the cartridge by a dividing wall 52, and a rear plunger 54 having opposing interior faces 56 and 58 to push a compound 100 or 110 in a respective portion of the interior 50 of the cartridge forward and out of the cartridge 10, and a pair of opposed angular sidewalls 60 and 62 ending in rear wall sidewalls 64 and 66 forming a seal against the interior sidewall 51 of the cartridge, each rear end 68 and 70 of the plunger 54 having a pocket 72 and 74 to receive a respective pushing piston from the dispensing pen 1000. Referring to FIG. 11, it can be seen that the chamber 50 is divided into two equal chambers 53 and 55 which contain different compounds which cannot come in contact with each other because the dividing wall 52 extends for the entire diameter interior "D1" and interior Length "L1" of the interior chamber 50 of the cartridge 10. For dual compounds where less is need of one of the two compounds, the dividing wall 52 is thicker on one side to reduce the volume of compound in the smaller chamber, the design of the plunger is modified to accommodate the revised sidewall 52. FIGS. 8 and 11 also show the frustum shaped front and threaded nozzle and threaded cap with a piercing tip. This portion of the cartridge 10 having a frustum shaped front leading to a threaded nozzle 32 with threads 20 and a frangible seal 26 and threaded cap 30 with interior mating threads 34, a piercing element 42 in an interior 40 of front 38 of cap 30.

From the outside, the single use single chamber cartridge 10 and the single use dual chamber cartridge 10 appear the same and are retained in the dispensing pen 1000 the same way.

In operation, the advancing shaft 1500 is incrementally moved forward by the present invention motor and gear box assembly illustrated in FIGS. 1 to 4 and discussed above. For the single chamber cartridge 10A, pushing piston 210A is used to engage the pocket 72A of the single-pocket plunger 54A used with a single chamber cartridge 10A and the electric motor and gearbox mechanism of the present invention moves the pushing piston 210S in the forward direction to push the plunger 54A forwardly to dispense a selected compound 100 out of the cartridge 10 through nozzle 32A. For the dual chamber cartridge 10, pushing pistons 210 and 220 are respectively used to engage a respective pocket 72 and 74 of the two-pocket plunger 54 used with the dual chamber cartridge 10 and the electric motor and gear box mechanism of the present invention moves the two pushing pistons 210 and 220 in the forward direction to push the plunger 54 forwardly to dispense a selected compound 100 and 110 out of the cartridge through nozzle 10. For the single chamber cartridge 10A, the ratchet mechanism incrementally moves the move the pushing piston 210S forwardly to move the plunger 54A forwardly to push the compounds 100 and 110 out of the cartridge 10 through nozzle 32. If the volume of the two compounds is different, the dividing wall 52 is thicker on one side to reduce the volume of compound in the smaller chamber, the design of the plunger is modified to accommodate the revised dividing wall 52.

Except for combining two compounds in a mixing nozzle, the operation after the compound is pushed out of the cartridge is the same.

Referring to FIGS. 9 and 11, there is respectively illustrated cross-sectional interior views of the single chamber cartridge 10A with a single compound 100 and a dual chamber cartridge with two compounds 100 and 110, the compound 100 and compounds 100 and 110 selected from the group consisting of a tooth whitening compound, a dental bonding and filling compound, and an adhesive compound in a sealed condition with the cap 30 threadedly retained onto the cartridge 10A and 10, and which cartridge is disposed of and replaced with a new single use cartridge for subsequent application of at least one compound. compound.

Figure 12:
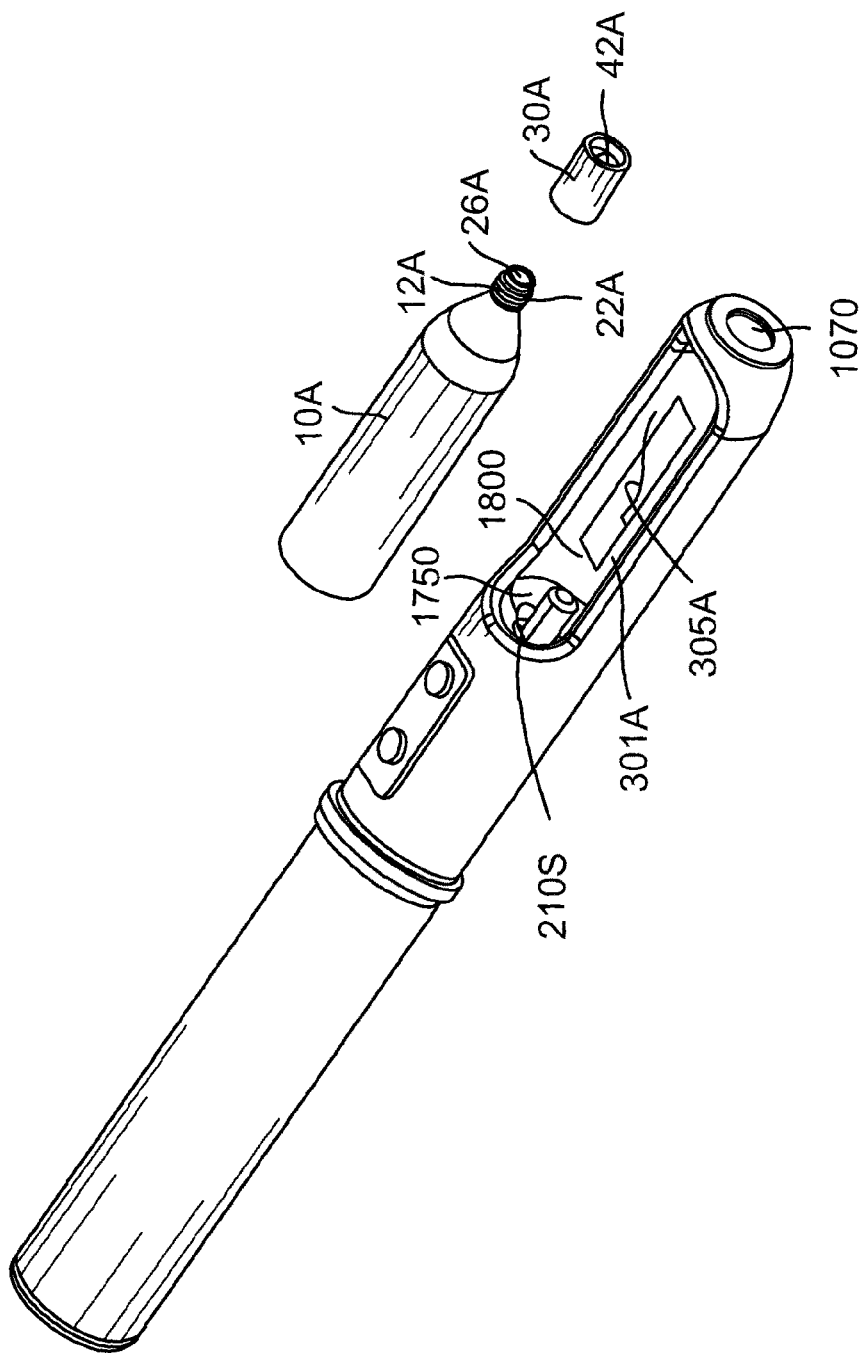
FIG. 12 is an exploded view illustrating a top left perspective view of the unidose dispensing pen with a single piston affixed to the advancing shaft mechanism illustrated in FIG. 1 within the dispensing pen, and a single use cartridge before it is inserted into the chamber with the dispensing pen and also illustrating a cartridge anti-rotation member within the chamber.

Referring to FIG. 12, there is illustrated a top right side view of the present invention unidose dispensing pen with the new electric motor and gear assembly 1200 illustrated in FIGS. 1 through 4 retained within the dispensing pen 1000 including illustrating the operating pushbutton 1600, the ratchet disengagement switch 1610, the open chamber 301A with an anti-rotation member 305A and the opening 1090. The cartridge 10A with cap 30A removed is inserted into chamber 301A with anti-rotation member 305A engaging anti-rotation slit 44 in the bottom surface of cartridge 10A with threads 22A protruding through opening 1090. Single pushing piston 210S is also illustrated.

Figure 13:
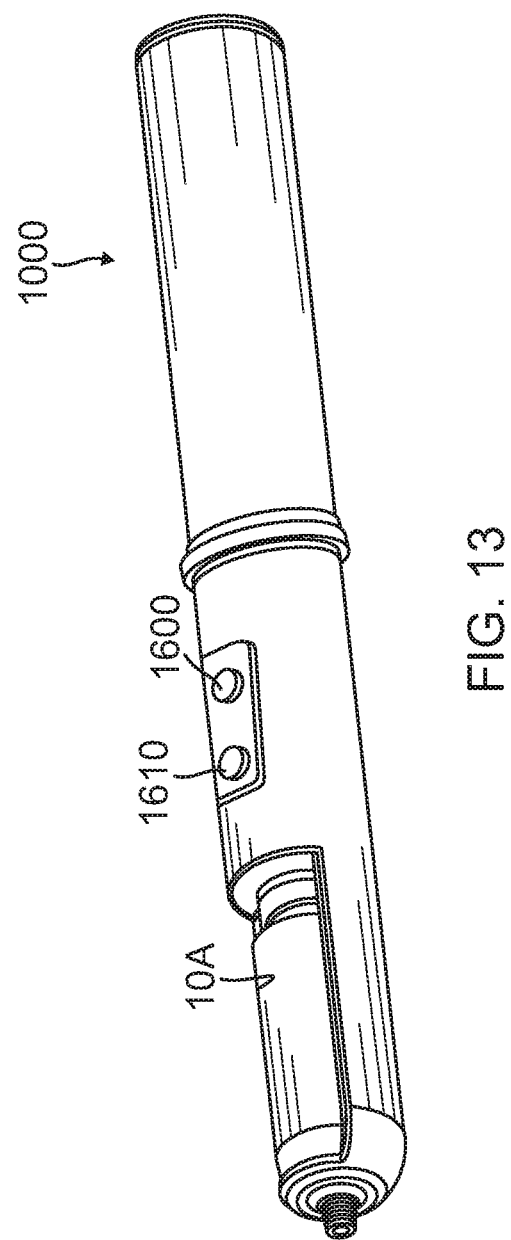
FIG. 13 is a top right side perspective view of the dispensing pen of the present invention as illustrated in FIG. 12, with the cartridge retained within the dispensing pen having the electric motor and gear assembly illustrated in FIGS. 1-4 with the single use cartridge retained within the interior chamber of the dispensing pen with the front portion of the top removed and the threaded nozzle of the single use cartridge protruding through the front opening of the dispensing pen.

FIG. 13 is a top left side perspective view of the present invention unidose dispensing pen 1000 with the new and novel mechanical ratchet dispensing mechanism 1400 illustrated in FIGS. 1 to 9 retained within the dispensing pen 1000 including illustrating the operating pushbutton 1600, the ratchet disengagement rotational switch 1610 and a single use cartridge 10A within the dispensing pen 1000.

Figure 14:
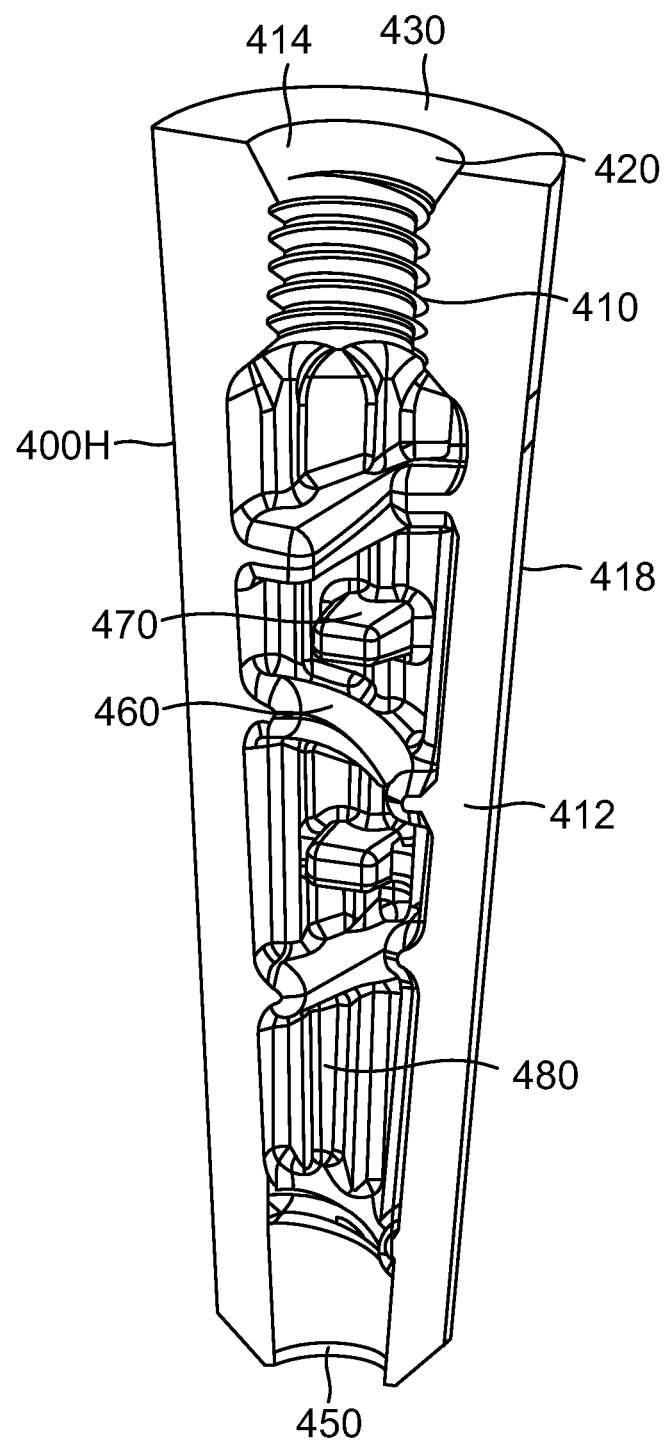
FIG. 14 is a longitudinal cross-sectional view of the mixing nozzle of the present invention used with a cartridge having a divided interior housing two separate compounds.
Figure 14A:
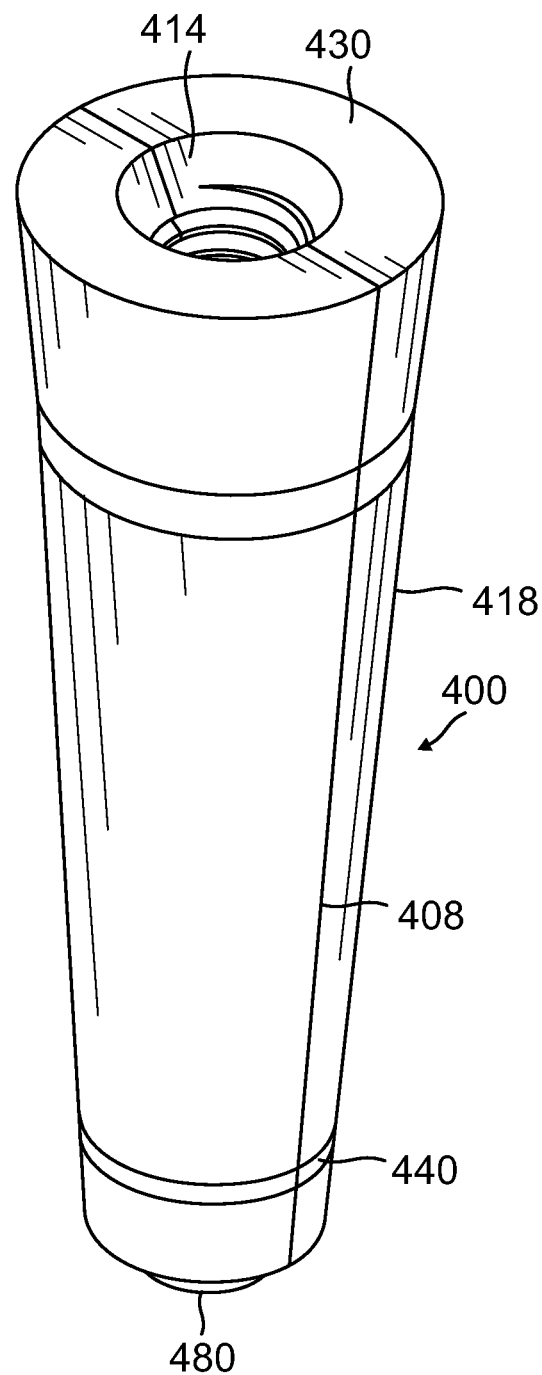
FIG. 14A is perspective view of the entire mixing nozzle including the two halves as illustrated in FIG. 14 sonic welded together at their respective mating surfaces at a location illustrated along a seam line to form an entire mixing tip.

Referring to FIGS. 14 and 14A, there is illustrated a cross-sectional view of one half 400H of the mixing nozzle 400 which is used with a dual chamber cartridge 10. The mixing nozzle 400 has internal threads 410 on its internal surface 420 adjacent its rear end 430 and on its external surface 418 external threads 440 adjacent its front end 450 and contains a multiplicity of semi-closed shelves 460 and also straight shelves 470 so that as the compounds 100 and 110 are driven through the mixing nozzle 400, the angular shelves 460 and the straight shelves 470 cause the compounds 100 and 110 to mix together and go through a series of angular shelves 460 and straight shelves 470 to make sure that the compounds are fully mixed when it gets to the opening 480 of the mixing chamber 400. A rear opening 414 permits the compounds 100 and 110 to enter the mixing nozzle 400 after it is screwed onto the threads 24 of tip 26 of cartridge 10. FIG. 14 illustrates one half of the mixing nozzle. The opposite half is a mirror image of half 400H. The two halves of sonic welded together along their longitudinal interior faces 412 to form a complete mixing nozzle 400 as illustrated in FIG. 14A. Referring to FIG. 14A, there is illustrated an exterior view of the mixing nozzle 400 with a seam line 408 to illustrate the location of the sonic weld.

A key innovation of the present invention mixing nozzle 400 is that it is comprised of internally built in shelves which thoroughly mix the compound portions as they are forced through the mixing nozzle. This is a major improvement over the prior art where an insert is placed into a chamber and compounds mixed through the insert which leads to less mixing and much more inefficiency in the mixing.

Figure 15:
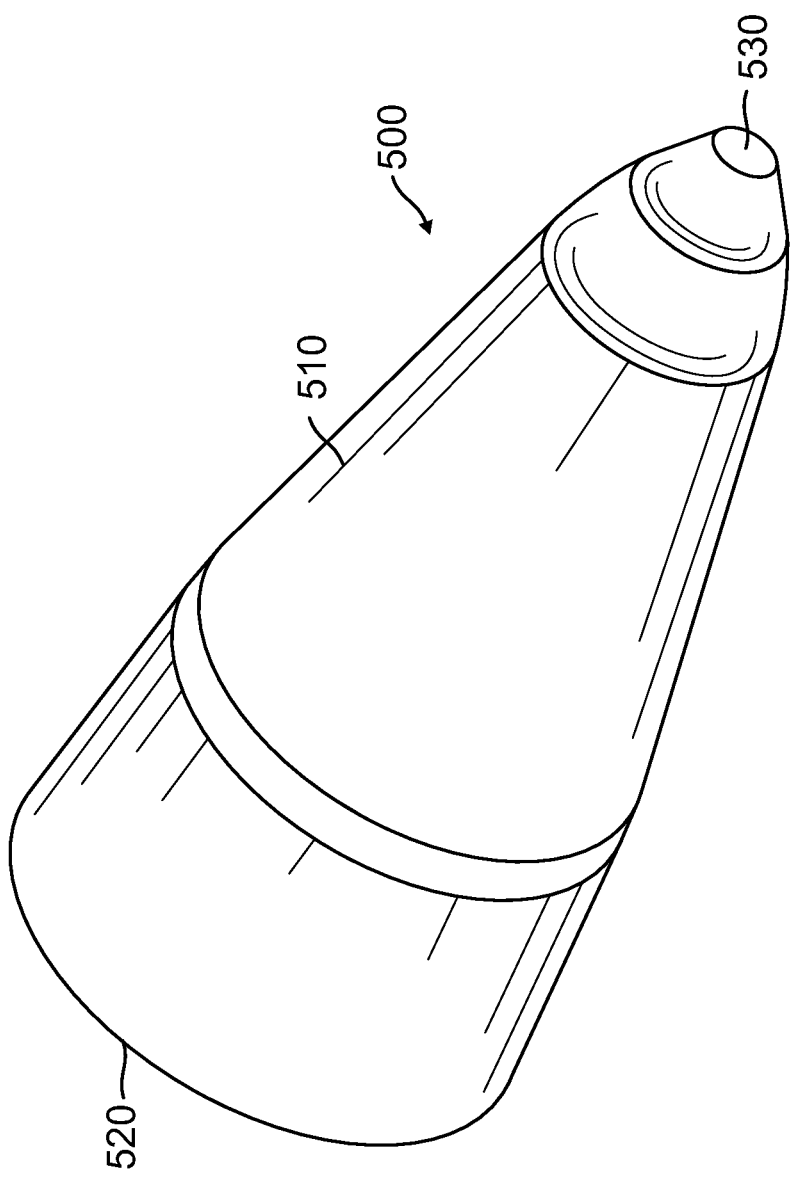
FIG. 15 is a perspective view of a straight dispensing nozzle used with a single chamber cartridge or used with a mixing tip and a dual chamber cartridge.
Figure 16:
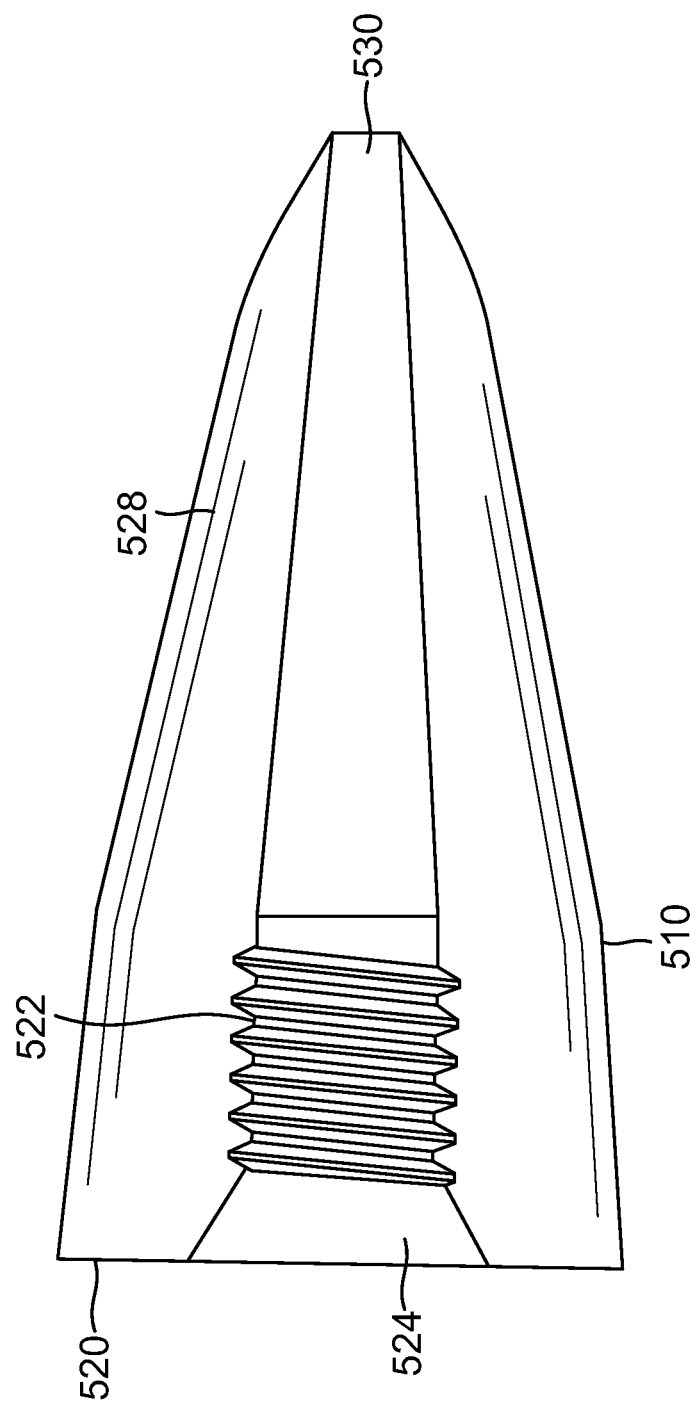
FIG. 16 is a cross-sectional view of the straight dispensing nozzle illustrated in FIG. 15.

Referring to FIGS. 15 and 16, there is illustrated a straight applicator 500 which contains an exterior surface 510 and an interior chamber 528 which has a widened end 520 with interior threads 522 surrounding a rear opening 524 that is either thread around the end of the mixing nozzle 400 or threaded around the threaded nozzle end of the compound cartridge 10A or 10, and a front opening 530 through which the compound is dispensed. The compound enters through rear opening 524 and exits through front opening 530.

Figure 17:
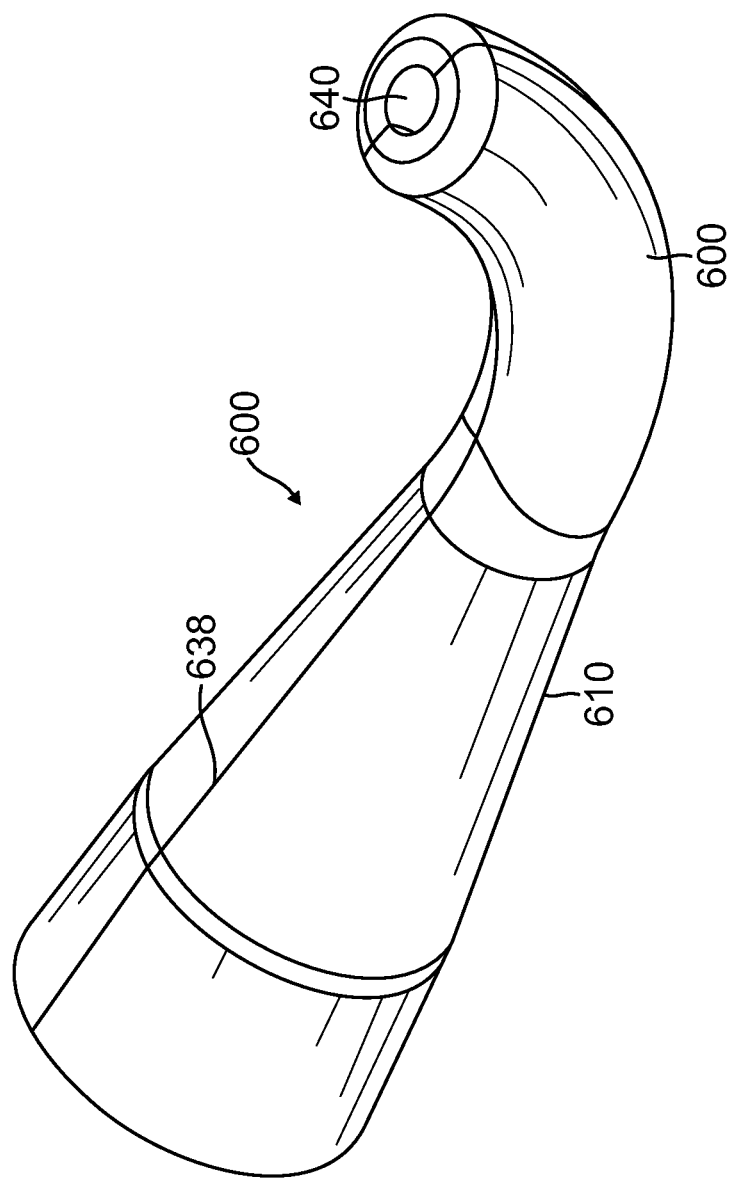
FIG. 17 is a perspective view of a bent horn tip dispensing nozzle used with a single chamber cartridge or used with a mixing tip dual chamber cartridge.
Figure 18:
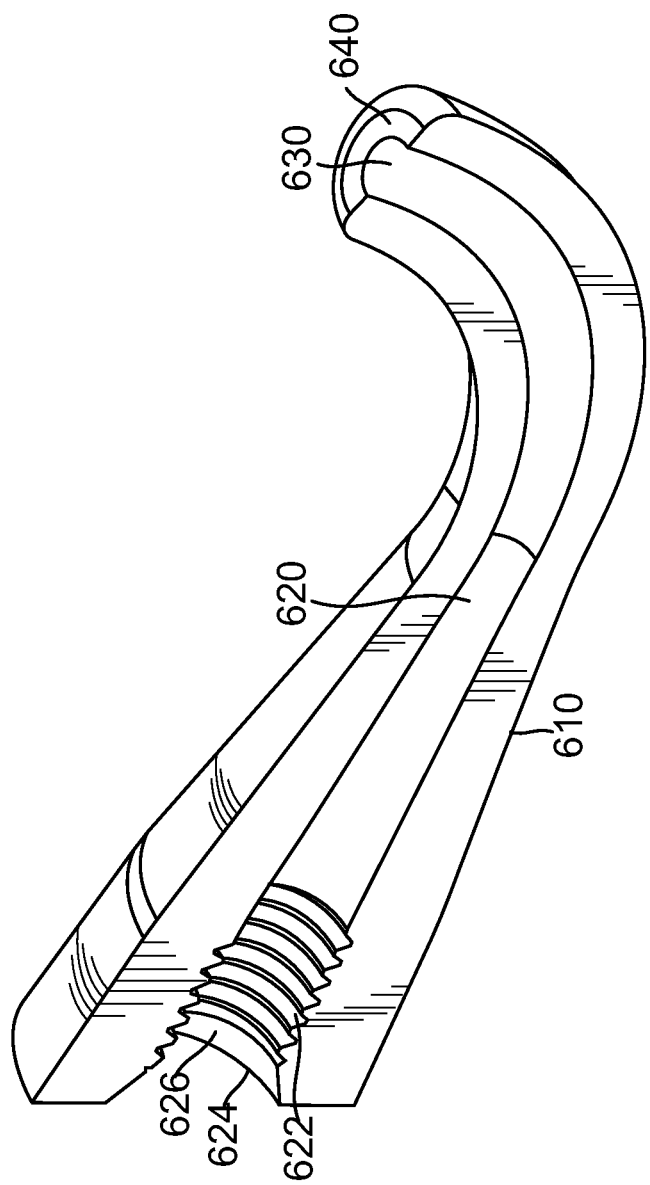
FIG. 18 is a cross-sectional view of the bent horn tip dispensing nozzle used with a single chamber cartridge or use with a mixing top dual chamber cartridge.

In an alternative embodiment illustrated in FIGS. 17 and 18, the applicator is a horn-shaped applicator 600 which has an exterior wall 610 and an interior chamber 620 which has a rear opening 624 and a rear interior wall 626 having threads 622 which can be threaded onto the end of the mixing nozzle tip or threaded onto the nozzle of a cartridge 10A or 10 and also has an opening 630 in front end 640 which is bent at an angle so that the tooth whitening compound can be applied to an interior surface of teeth or to teeth near the back of the patient's mouth, the dental bonding compound can be applied to rear teeth fillings and the adhesive compound can be applied at a rear area of objects to be bonded together. The selected compounds enter from rear opening 624 and exit through front opening 640.

Referring to FIG. 12 (before the cartridge 10 or 10A is inserted into the pen 1000) and FIG. 13 (after the cartridge 10 or 10A is inserted into the pen 1000) there is illustrated an exploded view showing how the mixing pen operates. The cartridge 10A containing the compound 100 is inserted into chamber 1800 near the front of the dispensing pen 1000 where the pocket 72A of the plunger 54A is retained against the single piston 210S and the front tip 12A of the cartridge 10A extends out of the opening 1910 in the front 1900 of the dispensing pen 1000. The anti-rotation slit 44 on the cartridge is placed into the anti-rotation member 1810 in chamber 1800 so the cartridge 10A will not rotate once inside the dispensing pen 1000. The sealing cap 30A is shown removed from the cartridge 10A. After the cartridge is inserted into the dispensing pen 1000, the cap 30A is used to penetrate the frangible seal 26A of the tip 22A of the cartridge 10A which extends out of the opening 1090 in the dispensing pen 1000 and thereafter either the straight applicator 500 or the horn-shaped applicator 600 is threaded onto the threads 24A of the cartridge 10A so that as the electric motor and gear mechanism causes advancing shaft 1500 and the piston 210S to move toward the front of the dispensing pen 1000, the piston 210S pushes on the pocket 74A of the plunger 54A causing the plunger 54A to move the compound 100 out of the cartridge 10A into an applicator. For the dual chamber interior cartridge 10 containing the compounds 100 and 110, the dual chamber cartridge 10A is inserted into chamber 1800 near the front 1900 of the dispensing pen 1000 where the pockets 72 and 74 of the plunger 54 are retained against the dual pistons 210 and 220 and the front nozzle 12 of the cartridge 10 extends out of the opening 1090 in the pen 1000. The anti-rotation slit 44 on the cartridge is placed into the anti-rotation member 1810 in chamber 1800 so the cartridge 10 will not rotate once inside the dispensing pen 1000. The sealing cap 30 is removed from the cartridge 10. After the cartridge is inserted into the dispensing pen 1000, the cap 30 is used to penetrate the frangible seal 26 of the tip 22 of the cartridge 10 which extends out of the opening 1090 in the dispensing pen 1000 and thereafter the mixing tip 400 is threaded onto the cartridge 10 and either the straight applicator 500 or the horn-shaped applicator 600 is threaded onto the mixing tip 400 so that as the electric motor and gear assembly cause the advancing shaft 1500 and the pistons 210 and 220 to move toward the front of the dispensing pen 1000, the pistons 210 and 220 push on the pockets 72 and 74 on the back of the plunger 54 causing the plunger 54 to move each compound 100 and 110 from each separate section of the cartridge 10 into the mixing tip 400 where the compounds 100 and 110 are mixed and then exit the mixing tip 400 into the applicator so that the mixed compounds which by way of example are tooth whitening compounds are either placed in a dental tray or placed on the patient's tooth.

Figure 19:
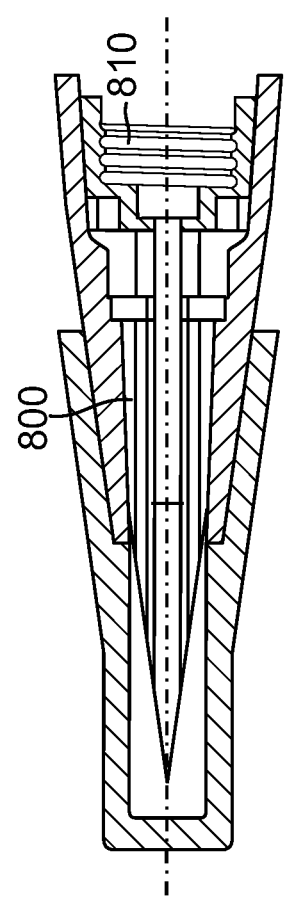
FIG. 19 is a cross-sectional view of an applicator brush.

Referring to FIG. 19 there is illustrated an applicator brush 800 which has interior mating threads 810 which are threaded onto the exterior threaded nozzle of the single use cartridge from which compound is dispensed onto the brush or onto the mixing tip nozzle for the dual chamber cartridge.

Figure 20:
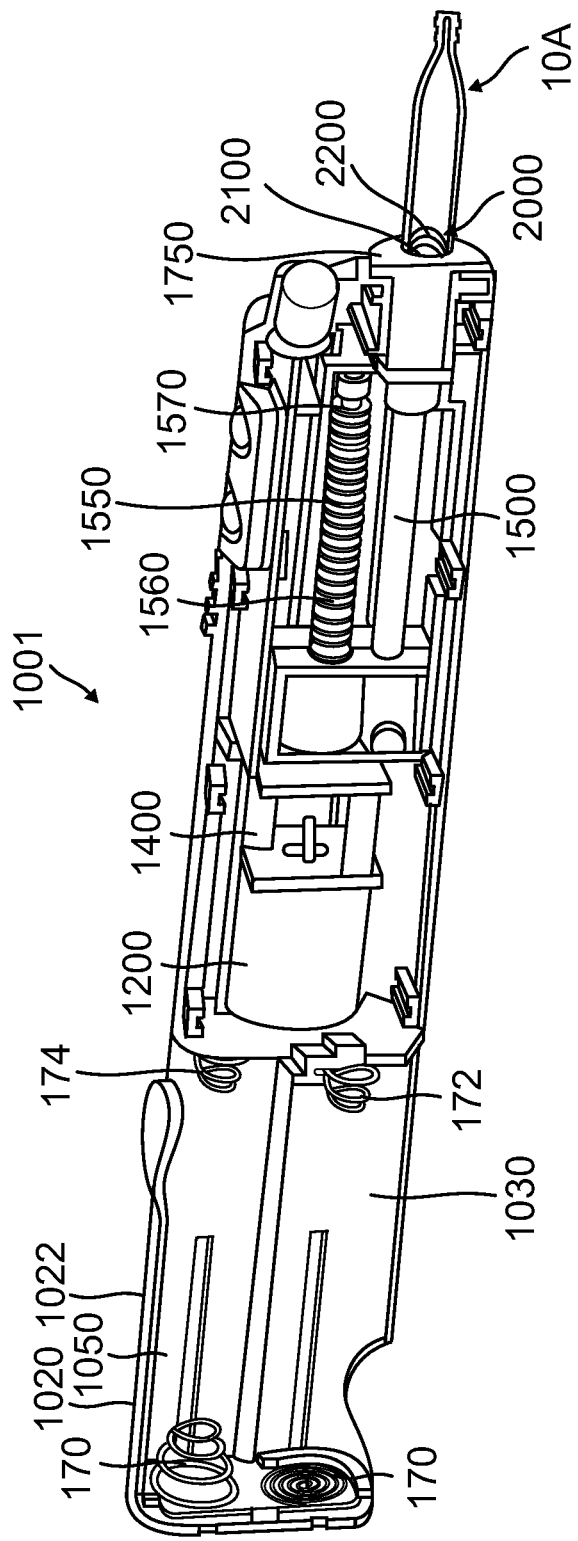
FIG. 20 is a side cross-sectional view of the dispensing pen which retains a single use cartridge within the dispensing pen and further discloses the present invention electrical motor mechanism connected to a gear mechanism which in turn is connected to a movement shaft having a multiplicity of teeth along the length of the movement shaft which interacts with mating teeth on a connector block which in turn is connected at a rear of an advancing shaft so that as the gear mechanism causes the movement shaft to move in a certain direction, the teeth of the movement shaft engage with the teeth of the connecting block and move the advancing shaft incrementally forward, which advancing shaft and movement shaft are shown in the starting position in FIG. 1 and a single use cartridge is illustrated with a sealing plunger, a first pushbutton switch, a second pushbutton switch, a programmable PCB board and a battery compartment at the rear of the dispensing pen; in this alternative variation, the cartridge is affixed to the front of the dispensing pen and has a mating member such as threads with an opening through which the advancing shaft extends.

FIG. 20 is a side cross-sectional view of the dispensing pen which retains a single use cartridge within the dispensing pen and further discloses the present invention electrical motor mechanism connected to a gear mechanism which in turn is connected to a movement shaft having a multiplicity of teeth along the length of the movement shaft which interacts with mating teeth on a connector block which in turn is connected at a rear of an advancing shaft so that as the gear mechanism causes the movement shaft to move in a certain direction, the teeth of the movement shaft engage with the teeth of the connecting block and move the advancing shaft incrementally forward, which advancing shaft and movement shaft are shown in the starting position in FIG. 1 and a single use cartridge is illustrated with a sealing plunger, a first pushbutton switch, a second pushbutton switch, a programmable PCB board and a battery compartment at the rear of the dispensing pen; in this alternative variation, the cartridge 10A is affixed to the front of the dispensing pen and has a mating member 2000 such as threads with an opening 2100 through which the advancing shaft 1500 extends. The difference in this variation is that instead of having the reusable cartridge 10 or 10A within a chamber within the dispensing pen, the dispensing pen 1001 has a front section wall 1750 having mating members 2000 which can be threads 2200 having an opening 2100 (see FIG. 5C) to receive the threads of a cartridge. The advancing shaft 1500 can then move through opening 2100 into the plunger of the cartridge affixed to the front of the dispensing pen.

Figure 21:
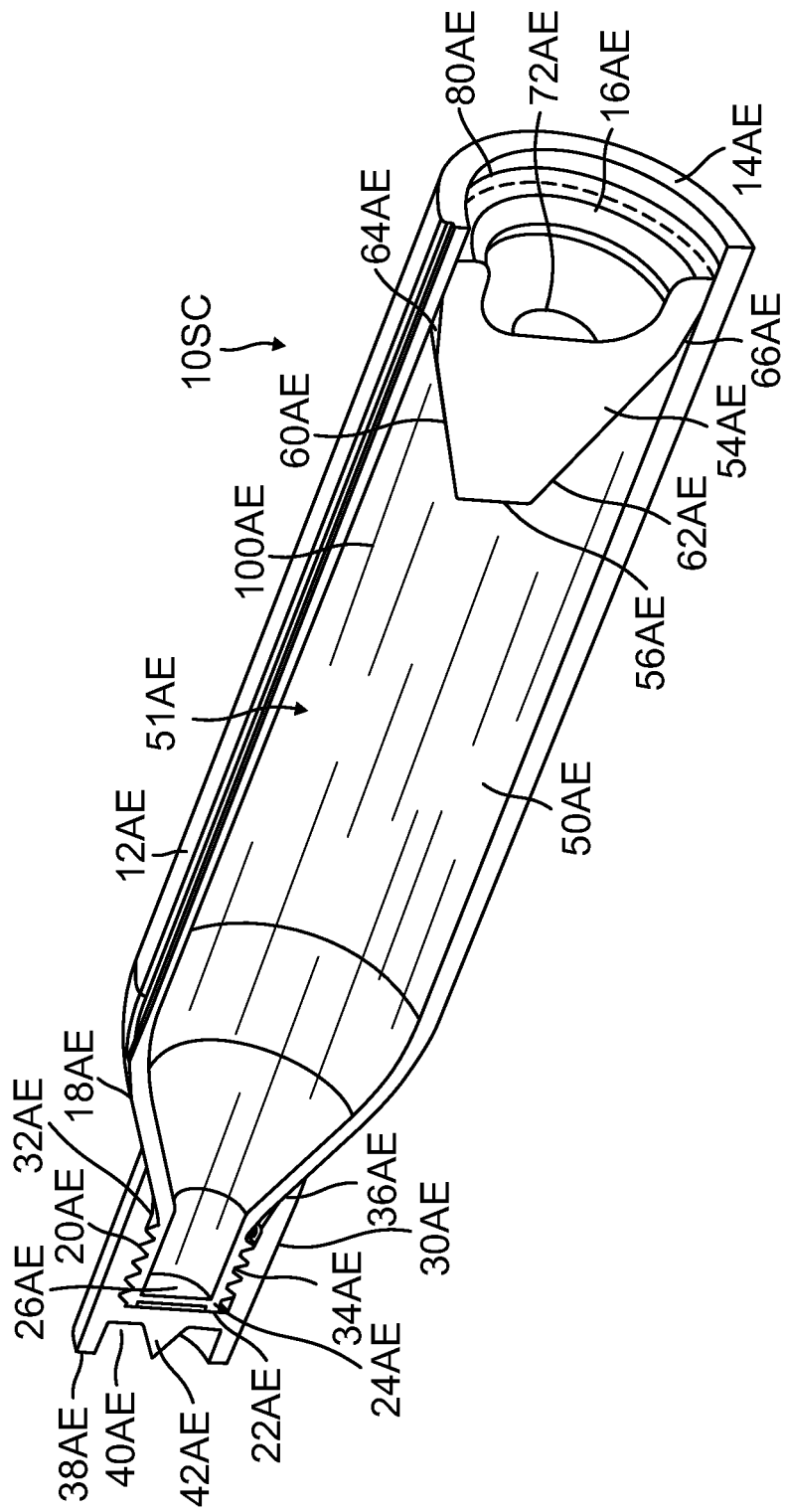
FIG. 21 is a side cross-sectional view of a first embodiment of the unidose single use cartridge illustrating a single interior chamber which retains one compound, and a rear plunger having an interior face to push the compound in the interior of the cartridge forward and out of the cartridge, and an angular sidewall ending in a rear wall forming a seal against the interior sidewall, the rear end of the plunger having a pocket to receive a single pushing piston, where the single chamber cartridge is retained on the front of the dispensing pen.

The variation of the reusable cartridge is the same as shown in FIGS. 9 and 11 but instead has internal threads thereon. Referring to FIG. 21, for the single use cartridge having a single chamber which will be described as 10-SC, the single use cartridge having a single interior chamber has interior threads 80AE which mate with the exterior threads 2200 at the front of the dispensing pen 2000. As a result, instead of being within the chamber, the single use cartridge with internal threads 80AE now is extending from the front of the dispensing pen 2000. The operating mechanism is the same as before with the single piston 210S affixed to the front of advancing shaft 1500 and moved forwardly in increments by the electrical motor assembly and gear assembly of the present invention to move pocket 72AE of pushing plunger 54AE. The compound 100AE is moved through the exterior cartridge 10A-SC through its exterior nozzle 32AE which also has threads 20AE and then dispensed into any of the applicators identified in FIGS. 15 to 19. The remaining components are numbered similar to the numbers in FIG. 9 but are numbered with AE.

Figure 22:
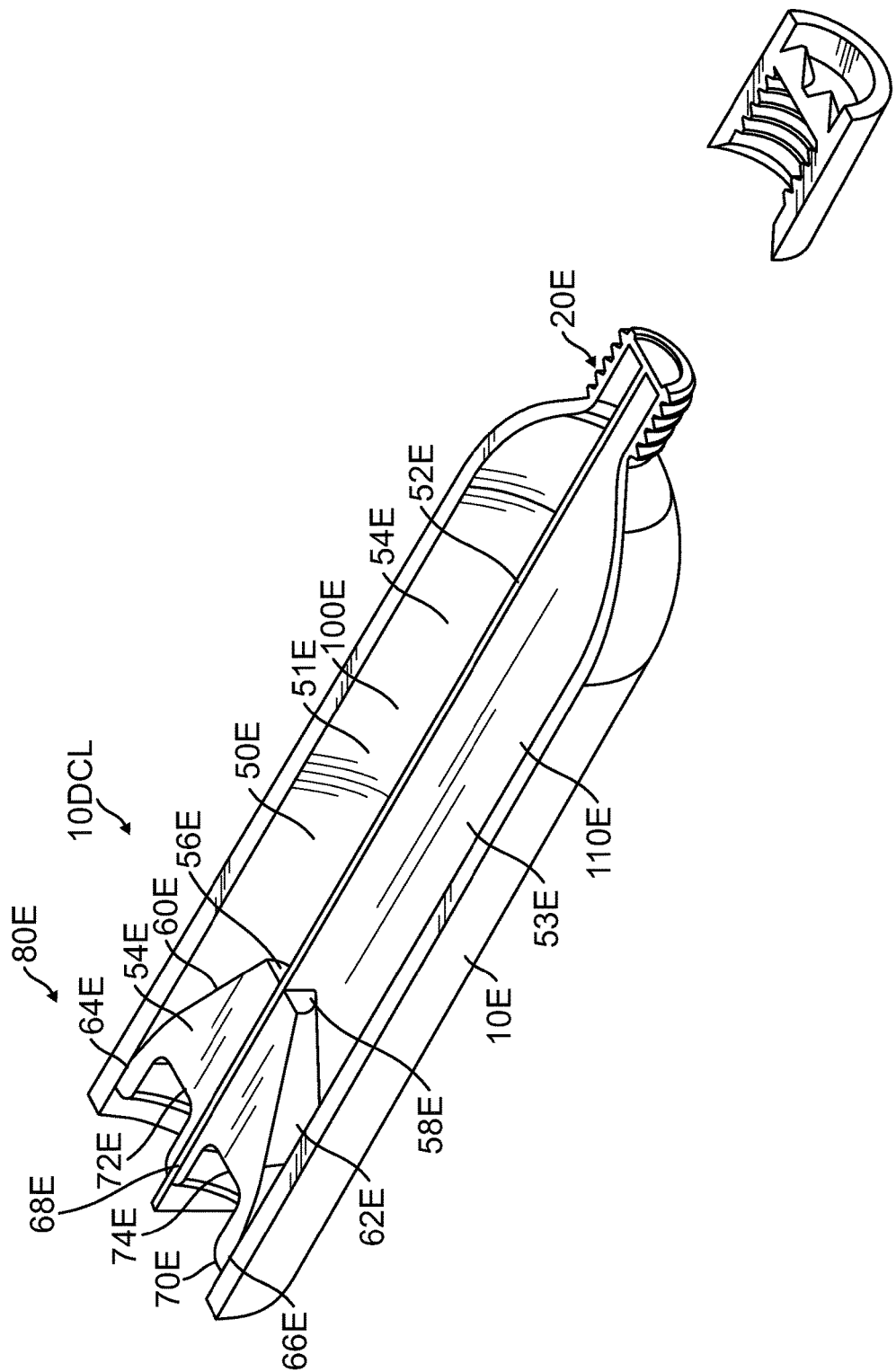
FIG. 22 is a top cutaway view of a second embodiment of the unidose single use cartridge having a divided interior chamber which retains two separate compounds which are separated from each other while in the cartridge by a dividing wall, and a rear plunger having opposing interior faces to push a compound in a respective portion of the interior of the cartridge forward and out of the cartridge, and a pair of opposed angular sidewalls ending in rear wall sidewalls forming a seal against the interior sidewall of the cartridge, each rear end of the plunger having a pocket to receive a respective pushing piston from the dispensing pen.

Alternatively, for a dual chamber cartridge, the mechanism described in FIG. 22 is threaded onto the front section 2100 of the dispensing pen 2000 so that advancing shaft 1500 with dual piston 210MMT affixed extends into a respective pocket 72E and 74E of the dual chamber cartridge which since it is an exterior cartridge will be referred to as 10-DCL. This exterior cartridge also has internal threads 80E which are threaded onto the mating threads 2200 of the dispensing pen connector 2000 so that the respective pistons 210 and 220 are moved into a respective pocket 72E and 74E of the exterior dual chamber reusable cartridge 10DCL so that the dual compound i100E and 110E are respectively pushed through the cartridge and out the exterior nozzle 20E and then into the mixing chamber 400 which is threaded onto the exterior surface of the cartridge with the same process as previously discussed. The remaining components are numbered similar to FIG. 11 with y "E" after each number.

The compound that is used with the present invention can be any multiplicity of compounds as previously discussed. The single use cartridge, whether it is retained within the dispensing pen or 10-SC which is exterior to the dispensing pen, can be any compound. If, by way of example, the compound 100 is a tooth whitening compound, then after being dispensed from the single use cartridge, the tooth whitening compound is placed in the dental tray where the tray is placed over the patient's teeth for a period of time or the tooth whitening compound is directly applied to the patient's teeth through a brush 800 as illustrated in FIG. 19. Alternatively, if it is a dual chamber single use cartridge 10, then two compounds 100 and 110 go through the chamber as tooth whitening compounds and then are combined together when they exit the nozzle 20E and go into the mixing chamber 400 where the two tooth whitening compounds are combined together in the mixing chamber 400 before they can be dispensed into a dental tray or other dental applicator.

Similarly, the compounds can be any type of products such as a glue, an adhesive, a powder, a gel, a cream, paint, cosmetics, lipstick, non-medicated cosmetics, medicated cosmetics, construction material compounds and virtually any other compound. If the compound does not need to be mixed with another compound, then a single use cartridge is used. If the compound needs to be mixed with another compound, then the dual chamber cartridge is used where they are respectively pushed through the dual chamber cartridge and then through the front nozzle and into the mixing nozzle where the two compounds are mixed together before they then can be applied to any one of the applicators or brushes set forth in FIGS. 15 to 18.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. An apparatus for removably retaining a unidose cartridge and dispensing at least one compound from the unidose cartridge, the apparatus comprising:
   a. a dispensing pen having a circumferential wall with an exterior surface and an interior surface, a rear interior chamber surrounded by a portion of an interior surface housing a source of electrical power electrically connected to an electric motor which in turn includes a rotatable shaft connected to a gear assembly, the gear assembly also connected to a moving shaft;

b. the moving shaft having a multiplicity of teeth thereon extending from a distal end of the moving shaft to a proximal end of the moving shaft, the multiplicity of teeth engaging mating teeth of a connecting block which in turn is connected to a proximal end of an advancing shaft which extends though the dispensing pen to the unidose cartridge retaining chamber in a front of the dispensing pen;

c. a pre-programmable printed electric circuit board connected to a first activation member and to a second activation member, the electric motor connected to the pre-programmable circuit board, when the first activation member is activated, the electric motor is activated, the gear assembly is activated and causes rotational motion of the moving shaft which in turn rotates the teeth on the moving shaft which engages the teeth on the connecting block which in turn moves the connecting block in a direction toward the front of the dispensing pen and concurrently causes the advancing shaft to move toward the front of the dispensing pen; and d. the dispensing pen including the unidose cartridge retaining chamber located between an interior dividing wall and a front of the dispensing pen, the unidose cartridge retaining chamber surrounded by a portion of the interior surface of the dispensing pen and the exterior wall of the dispensing pen, an interior dividing wall separating the advancing shaft and the movement shaft from the unidose cartridge retaining chamber, the dispensing pen including a front wall with a front opening.

2. The apparatus in accordance with claim 1, further comprising:
a. a light which is illuminated when the first activation member is activated and causes the advancing shaft to move toward the front of the dispensing pen; and
b. the light is illuminated when the second activation member is activated while the movement shaft causes the activation shaft return to its starting position.

3. The apparatus in accordance with claim 1, further comprising:
a. the first activation member is a pushbutton extending through and accessible from the outer surface of the dispensing pen; and
b. the second activation member is a pushbutton extending through and accessible from the outer surface of the dispensing pen.

4. The apparatus in accordance with claim 1, further comprising: the source of electric power is selected from the group consisting of at least one non-rechargeable battery and at least one rechargeable battery.

5. An apparatus in accordance with claim 1, further comprising:
a. the unidose cartridge received in the unidose cartridge receiving chamber of the dispensing pen includes an exterior surface which surrounds an interior circumferential wall surrounding an interior chamber and a rear opening leading to the interior chamber, a compound retained within the interior chamber, a plunger having a front interior surface aligned with the interior chamber and having sidewalls which serve as a seal against the interior circumferential wall to prevent the compound from flowing out of the rear opening, the plunger having a rear pocket, the exterior surface leading to a connecting section extending from a body of the exterior surface to a nozzle having a cylindrical surface extending from the connecting section to a dispensing nozzle tip having threads on an exterior surface of the dispensing nozzle tip and a frangible seal on a front end of the dispensing nozzle tip to retain the compound in a sealed condition within the interior chamber, a threaded cylindrical sealing cap with an interior surface with threads adjacent the rear of the sealing cap and a front end with an interior chamber having a piercing tooth within the interior which extends inwardly from the front end of the sealing cap, the sealing cap threaded onto the threads of the nozzle tip, and after the sealing cap is unthreaded from the nozzle tip of the cartridge, the unidose cartridge is inserted into and retained in the unidose cartridge retaining chamber with the threaded nozzle extending through the opening in the front of the unidose pen, the piercing tooth is used to penetrate the frangible seal so that the nozzle tip is opened to enable the compound to be dispensed from the interior of the unidose cartridge; and b. a single pushing piston affixed onto the distal end of the advancing shaft and aligned with the pocket of the plunger, the activated first activation member causing the turned on electric motor and first gear assembly to move the moving shaft which in turn moves the advancing shaft and attached single piston to incrementally move toward the front of the dispensing pen which in turn causes the pushing piston to move the plunger toward the opening in the nozzle to dispense the compound out of the single use unidose cartridge.

6. The apparatus in accordance with claim 5, further comprising:
a. an anti-rotation member extending from a portion of the interior surface at the unidose cartridge retaining chamber and extending into the unidose cartridge retaining chamber; and
b. a mating anti-rotation member in a sidewall of the unidose cartridge to receive the anti-rotation member from the dispensing pen.

7. The apparatus in accordance with claim 5, further comprising:
a. an applicator selected from the group consisting of a straight applicator, a horn shaped applicator and an applicator brush;
b. the straight applicator includes an exterior surface and an interior chamber which has a widened end with interior threads surrounding a rear opening by which the straight applicator is threaded onto the threads of the single use cartridge and then the compound is pushed out a front opening in the straight applicator;
c. the horn-shaped applicator which has an exterior wall and an interior chamber which has a rear opening and a rear interior wall having threads which are threaded onto the threads of the single use unidose cartridge and then the compound is pushed out of a front opening in the single use unidose cartridge; and
d. the applicator brush includes interior mating threads which are threaded onto the threads of the single use cartridge and then the compound is pushed onto the applicator brush.

8. The apparatus in accordance with claim 5, further comprising: the compound is selected from the group consisting of tooth whitening compounds, dental bonding and filling compounds, adhesives including as glue, finely ground powder, jells, creams, paints, cosmetics, lipstick, non-medicated cosmetics, medicated cosmetics, nail polish and construction material compounds.

9. The apparatus in accordance with claim 1, further comprising:

a. the unidose cartridge received in the unidose cartridge receiving chamber of the dispensing pen includes an exterior surface which surrounds an interior circumferential wall surrounding interior dual chambers separated by an interior longitudinal dividing wall and a rear opening leading to the interior dual chambers, two compounds with a respective compound retained within a respective one chamber of the dual interior chambers and separated by the interior longitudinal dividing wall, a plunger having a front interior surfaces aligned with a respective one chamber and having sidewalls which serve as a seal against the interior circumferential wall to prevent the compounds from flowing out of the rear opening, the plunger having a pair of rear spaced apart pockets respectively aligned with a respective one of the dual chambers, the exterior surface leading to a connecting section extending from a body of the exterior surface to a nozzle having a cylindrical surface extending from the connecting section to a dispensing nozzle tip having threads on an exterior surface of the dispensing nozzle tip and a frangible seal on a front end of the dispensing nozzle tip to retain the compounds in a sealed condition within the dual interior chambers, a threaded cylindrical sealing cap with an interior surface with threads adjacent the rear of the sealing cap and a front end with an interior chamber having a piercing tooth within the interior which extends inwardly from the front end of the sealing cap, the sealing cap threaded onto the threads of the nozzle tip, and after the sealing cap is unthreaded from the nozzle tip of the cartridge, the piercing tooth is used to penetrate the frangible seal so that the nozzle tip is opened to enable the compounds to be dispensed from the interior of the single use cartridge; and b. dual pushing pistons affixed onto the distal end of the advancing shaft and aligned with the pockets of the plunger, the activated first activation member causing the turned on electric motor and first gear assembly to move the moving shaft which in turn moves the advancing shaft and attached dual pistons to incrementally move toward the front of the dispensing pen which in turn causes a respective one of the dual pushing pistons to incrementally move a respective one of the pair of rear spaced apart pockets respectively aligned with a respective one of the dual chambers toward the opening in the nozzle to dispense the compounds out of the single use unidose cartridge.

10. The apparatus in accordance with claim 9, further comprising: a mixing nozzle having internal threads on an internal surface adjacent a rear open rear end of the mixing nozzle by which the mixing nozzle is threaded onto the threads of the nozzle tip of the single use cartridge, and external threads on a front surface adjacent a front end of the mixing nozzle, an interior of the mixing nozzle including a multiplicity of angular shelves and straight shelves formed into the interior of the mixing nozzle in longitudinally arranged sets so that as the compounds are driven through the mixing nozzle, the angular shelves and the straight shelves cause the compounds to mix together and go through a series of angular shelves and straight shelves to completely mix the compounds before the compounds are pushed to a front opening in the mixing nozzle.

11. The apparatus in accordance with claim 9, further comprising:

a. an applicator selected from the group consisting of a straight applicator, a horn shaped applicator and an applicator brush;

b. the straight applicator includes an exterior surface and an interior chamber which has a widened end with interior threads surrounding a rear opening by which the straight applicator is threaded onto the exterior threads of the mixing nozzle so that compounds are pushed out of the single use cartridge into the mixing nozzle and then mixed compounds are pushed out of the mixing nozzle into the straight applicator and then pushed out a front opening in the straight applicator;

c. the horn-shaped applicator which has an exterior wall and an interior chamber which has a rear opening and a rear interior wall having threads which are threaded onto the exterior threads of the mixing nozzle so that compounds are pushed out of the single use cartridge into the mixing nozzle and then mixed compounds are pushed out of the mixing nozzle into the horn shaped applicator which is bent at an angle so that the compounds are pushed out of a front opening in the horn shaped applicator; and d. the applicator brush includes interior mating threads which are threaded onto the exterior threads of the mixing nozzle so that the compounds are pushed out of the single use cartridge into the mixing nozzle and then mixed compounds are pushed out of the mixing nozzle onto the applicator brush.

12. The apparatus in accordance with claim 9, further comprising: each of the compounds are respectively selected from the group consisting of tooth whitening compounds, dental bonding and filling compounds, adhesives including glue, finely ground powder, jells, creams, paints, cosmetics, lipstick, non-medicated cosmetics, medicated cosmetics, nail polish, and construction material compounds.

13. An apparatus for removably retaining a single use cartridge and dispensing at least one compound from the single use cartridge, the apparatus comprising:

a. a dispensing pen having a circumferential wall with an exterior surface and an interior surface, a rear interior chamber surrounded by a portion of an interior surface housing a source of electrical power electrically connected to an electric motor which in turn includes a rotatable shaft connected to a gear assembly, the gear assembly also connected to a moving shaft;

b. the moving shaft having a multiplicity of teeth thereon extending from a distal end of the moving shaft to a proximal end of the moving shaft, the multiplicity of teeth engaging mating teeth of a connecting block which in turn is connected to a proximal end of an advancing shaft which extends though the dispensing pen to a cartridge retaining chamber in a front of the dispensing pen through an opening in a cartridge retaining member affixed to a front of the dispensing pen;

c. a pre-programmable printed electric circuit board connected to a first activation member and to a second activation member, the electric motor connected to the pre-programmable circuit board, when the first activation member is activated, the electric motor is activated, the gear assembly is activated and causes rotational motion of the moving shaft which in turn rotates the teeth on the moving shaft which engages the teeth on the connecting block which in turn moves the connecting block in a direction toward the front of the dispensing pen and concurrently causes the advancing shaft to move toward the front of the dispensing pen and through the opening in the cartridge retaining member; and d. the cartridge retaining member having an exterior surface including mating threads.

14. The apparatus in accordance with claim 13, further comprising:
   a. a light which is illuminated when the first activation member is activated and causes the advancing shaft to move toward the front of the dispensing pen; and
   b. the light is illuminated when the second activation member is activated while the movement shaft causes the activation shaft return to its starting position.

15. The apparatus in accordance with claim 13, further comprising:
   a. the first activation member is a pushbutton extending through and accessible from the outer surface of the dispensing pen; and
   b. the second activation member is a pushbutton extending through and accessible from the outer surface of the dispensing pen.

16. The apparatus in accordance with claim 13, further comprising: the source of electric power is selected from the group consisting of at least one non-rechargeable battery and at least one rechargeable battery.

17. An apparatus in accordance with claim 13, further comprising:
   a. the cartridge includes an exterior surface which surrounds an interior circumferential wall surrounding an interior chamber and a rear opening leading to the interior chamber, mating threaded members within an interior wall on the interior chamber surrounding the interior wall at the location adjacent the rear opening and mating with and retained by the mating threads of the cartridge retaining member of the dispensing pen so that the unidose cartridge is retained on, exterior to and in front of the dispensing pen, the
   compound retained within the interior chamber, a plunger having a front interior surface aligned with the interior chamber and having sidewalls which serve as a seal against the interior circumferential wall to prevent the compound from flowing out of the rear opening, the plunger having a rear pocket, the exterior surface leading to a connecting section extending from a body of the exterior surface to a nozzle having a cylindrical surface extending from the connecting section to a dispensing nozzle tip having threads on an exterior surface of the dispensing nozzle tip and a frangible seal on a front end of the dispensing nozzle tip to retain the compound in a sealed condition within the interior chamber, a threaded cylindrical sealing cap with an interior surface with threads adjacent the rear of the sealing cap and a front end with an interior chamber having a piercing tooth within the interior which extends inwardly from the front end of the sealing cap, the sealing cap threaded onto the threads of the nozzle tip, and after the sealing cap is unthreaded from the nozzle tip of the cartridge, the cartridge is inserted into and retained in the cartridge retaining chamber with the threaded nozzle extending through the opening in the front of the unidose pen, the piercing tooth is used to penetrate the frangible seal so that the nozzle tip is opened to enable the compound to be dispensed from the interior of the unidose cartridge; and
   b. a single pushing piston affixed onto the distal end of the advancing shaft and aligned with the pocket of the plunger, the activated first activation member causing the turned on electric motor and gear assembly to move the moving shaft which in turn moves the advancing shaft and attached single piston to incrementally move toward the front of the dispensing pen which in turn causes the pushing piston to move the plunger toward the opening in the nozzle to dispense the compound out of the single use unidose cartridge.

18. The apparatus in accordance with claim 17, further comprising:
   a. an applicator selected from the group consisting of a straight applicator, a horn shaped applicator and an applicator brush;
   b. the straight applicator includes an exterior surface and an interior chamber which has a widened end with interior threads surrounding a rear opening by which the straight applicator is threaded onto the threads of the single use cartridge and then the compound is pushed out a front opening in the straight applicator;
   c. the horn-shaped applicator which has an exterior wall and an interior chamber which has a rear openings and a rear interior wall having threads which are threaded onto the threads of the single use unidose cartridge and then the compound is pushed out of a front opening in the single use unidose cartridge; and
   d. the applicator brush includes interior mating threads which are threaded onto the threads of the single use cartridge and then the compound is pushed onto the applicator brush.

19. The apparatus in accordance with claim 17, further comprising: the compound is selected from the group consisting of tooth whitening compounds, dental bonding and filling compounds, adhesives including as glue, finely ground powder, jells, creams, paints, cosmetics, lipstick, non-medicated cosmetics, medicated cosmetics, nail polish and construction material compounds.

20. The apparatus in accordance with claim 17, further comprising:
   a. the cartridge including an exterior surface which surrounds an exterior circumferential wall surrounding an interior chamber and a rear opening leading to the interior chamber, mating threaded members within an interior wall on the interior chamber surrounding the interior wall at the location adjacent the rear opening and mating with and retained by the mating threads of the cartridge retaining member of the dispensing pen so that the cartridge is retained on, exterior to and in front of the dispensing pen, the cartridge having interior dual chambers separated by an interior longitudinal dividing wall with two compounds with a respective compound retained within a respective one chamber of the dual interior chambers, a plunger having a front interior surfaces aligned with a respective one chamber and having sidewalls which serve as a seal against the interior circumferential wall to prevent the compounds from flowing out of the rear opening, the plunger having a pair of rear spaced apart pockets respectively aligned with a respective one of the dual chambers, the exterior surface leading to a connecting section extending from a body of the exterior surface to a nozzle having a cylindrical surface extending from the connecting section to a dispensing nozzle tip having threads on an exterior surface of the dispensing nozzle tip and a frangible seal on a front end of the dispensing nozzle tip to retain the compounds in a sealed condition within the dual interior chambers, a threaded cylindrical sealing cap with an interior surface with threads adjacent the rear of the sealing cap and a front end with an interior chamber having a piercing tooth within the interior which extends inwardly from the front end of the sealing cap, the sealing cap threaded onto the threads of the nozzle tip, and after the sealing cap is unthreaded from the nozzle tip of the cartridge, the piercing tooth is used to penetrate the frangible seal so that the nozzle tip is opened to enable the compounds to be dispensed from the interior of the single use cartridge; and b. a dual pushing pistons affixed onto the distal end of the advancing shaft and aligned with the pockets of the plunger, the activated first activation member causing the turned on electric motor and first gear assembly to move the moving shaft which in turn moves the advancing shaft and attached dual pistons to incrementally move toward the front of the dispensing pen which in turn causes a respective one of the dual pushing pistons to incrementally move a respective one of the pair of rear spaced apart pockets respectively aligned with a respective one of the dual chambers toward the opening in the nozzle to dispense the compounds out of the single use cartridge.

21. The apparatus in accordance with claim 20, further comprising: a mixing nozzle having internal threads on an internal surface adjacent a rear open rear end of the mixing nozzle by which the mixing nozzle is threaded onto the threads of the nozzle tip of the single use cartridge, and external threads on a front surface adjacent a front end of the mixing nozzle, an interior of the mixing nozzle including a multiplicity of angular shelves and straight shelves formed into the interior of the mixing nozzle in longitudinally arranged sets so that as the compounds are driven through the mixing nozzle, the angular shelves and the straight shelves cause the compounds to mix together and go through a series of angular shelves and straight shelves to completely mix the compounds before the compounds are pushed to a front opening in the mixing nozzle.

22. The apparatus in accordance with claim 20, further comprising:

a. an applicator selected from the group consisting of a straight applicator, a horn shaped applicator and an applicator brush;
b. the straight applicator includes an exterior surface and an interior chamber which has a widened end with interior threads surrounding a rear opening by which the straight applicator is threaded onto the exterior threads of the mixing nozzle so that compounds are pushed out of the single use cartridge into the mixing nozzle and then mixed compounds are pushed out of the mixing nozzle into the straight applicator and then pushed out a front opening in the straight applicator;
c. the horn-shaped applicator which has an exterior wall and an interior chamber which has a rear opening and a rear interior wall having threads which are threaded onto the exterior threads of the mixing nozzle so that compounds are pushed out of the single use cartridge into the mixing nozzle and then mixed compounds are pushed out of the mixing nozzle into the horn shaped applicator which is bent at an angle so that the compounds are pushed out of a front opening in the horn shaped applicator; and
d. the applicator brush includes interior mating threads which are threaded onto the exterior threads of the mixing nozzle so that the compounds are pushed out of the single use cartridge into the mixing nozzle and then mixed compounds are pushed out of the mixing nozzle onto the applicator brush.

23. The apparatus in accordance with claim 20 further comprising: each of the compounds are respectively selected from the group consisting of tooth whitening compounds, dental bonding and filling compounds, adhesives including glue, finely ground powder, jells, creams, paints, cosmetics, lipstick, non-medicated cosmetics, medicated cosmetics, nail polish, and construction material compounds.

\* \* \* \* \*